(12) United States Patent
Qu et al.

(10) Patent No.: US 11,913,022 B2
(45) Date of Patent: Feb. 27, 2024

(54) IN VITRO INDUCTION OF MAMMARY-LIKE DIFFERENTIATION FROM HUMAN PLURIPOTENT STEM CELLS

(71) Applicant: Cedars-Sinai Medical Center, Los Angeles, CA (US)

(72) Inventors: Ying Qu, Los Angeles, CA (US); Xiaojiang Cui, Arcadia, CA (US); Dhruv Sareen, Porter Ranch, CA (US); Armando E. Giuliano, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 504 days.

(21) Appl. No.: 16/480,778

(22) PCT Filed: Jan. 25, 2018

(86) PCT No.: PCT/US2018/015318
§ 371 (c)(1),
(2) Date: Jul. 25, 2019

(87) PCT Pub. No.: WO2018/140647
PCT Pub. Date: Aug. 2, 2018

(65) Prior Publication Data
US 2020/0002671 A1 Jan. 2, 2020

Related U.S. Application Data

(60) Provisional application No. 62/450,484, filed on Jan. 25, 2017.

(51) Int. Cl.
*A61K 35/55* (2015.01)
*C12N 5/071* (2010.01)
*C12N 5/074* (2010.01)

(52) U.S. Cl.
CPC ............ *C12N 5/0631* (2013.01); *A61K 35/55* (2013.01); *C12N 5/0696* (2013.01); *C12N 2506/45* (2013.01); *C12N 2533/54* (2013.01); *C12N 2533/90* (2013.01)

(58) Field of Classification Search
CPC .......................... C12N 5/0631; C12N 5/0696; C12N 2506/45; C12N 2533/54; C12N 2533/90; A61K 35/55
See application file for complete search history.

(56) References Cited

U.S. PATENT DOCUMENTS

| 6,300,080 | B1 | 10/2001 | Brenner et al. |
| 7,989,197 | B2 | 8/2011 | Yoo et al. |
| 8,647,861 | B2 | 2/2014 | Ingber et al. |
| 9,790,470 | B2 | 10/2017 | Vallier et al. |
| 10,174,289 | B2 | 1/2019 | Wells et al. |
| 11,326,149 | B2 | 5/2022 | Kerns et al. |
| 2004/0247571 | A1 | 12/2004 | Meijer et al. |
| 2007/0077649 | A1 | 4/2007 | Sammak et al. |
| 2007/0128722 | A1 | 6/2007 | Lin |
| 2007/0281353 | A1 | 12/2007 | Vacanti et al. |
| 2008/0044847 | A1 | 2/2008 | Shusta et al. |
| 2008/0132445 | A1 | 6/2008 | Ormandy et al. |
| 2008/0305086 | A1 | 12/2008 | Poole |
| 2009/0075374 | A1* | 3/2009 | Palecek ................ C12N 5/0629 435/366 |
| 2009/0123383 | A1 | 5/2009 | Frangioni |
| 2009/0214649 | A1 | 8/2009 | Gazit et al. |
| 2009/0258337 | A1 | 10/2009 | Yagi |
| 2009/0317852 | A1 | 12/2009 | Parker et al. |
| 2009/0324559 | A1 | 12/2009 | Sakurada et al. |
| 2010/0136690 | A1 | 6/2010 | Sundstorm et al. |

(Continued)

FOREIGN PATENT DOCUMENTS

| AU | 2015204375 A1 | 8/2015 |
| AU | 2016341880 A1 | 5/2018 |

(Continued)

OTHER PUBLICATIONS

Hens et al ("BMP4 and PTHrP interact to stimulate ductal outgrowth during embryonic mammary development and to inhibit hair follicle induction," Development 134, 1221-1230 (2007)).*

(Continued)

*Primary Examiner* — Anoop K Singh
*Assistant Examiner* — Suzanne E Ziska
(74) *Attorney, Agent, or Firm* — Nixon Peabody LLP

(57) ABSTRACT

Human induced pluripotent stem cells (iPSCs) can give rise to multiple cell types and hold great promise in regenerative medicine and disease modeling applications. The Inventors herein developed a reliable two-step protocol to generate human mammary-like organoids from iPSCs. Non-neural ectoderm cell-containing spheres, referred to as mEBs, were first differentiated and enriched from iPSCs using MammoCult medium. Gene expression profile analysis suggested that mammary gland function-associated signaling pathways were hallmarks of 10-d differentiated mEBs. The Inventors generated mammary-like organoids from 10-d mEBs using 3D floating mixed gel culture and a three-stage differentiation procedure. These organoids expressed common breast tissue, luminal, and basal markers, including estrogen receptor, and could be induced to produce milk protein. These results demonstrate that human iPSCs can be directed in vitro toward mammary lineage differentiation.

19 Claims, 23 Drawing Sheets

(56) References Cited

U.S. PATENT DOCUMENTS

| | | |
|---|---|---|
| 2011/0064700 A1 | 3/2011 | Cardozo et al. |
| 2011/0097796 A1 | 4/2011 | Loa |
| 2011/0111499 A1 | 5/2011 | Torihashi |
| 2011/0245307 A1 | 10/2011 | Alkon |
| 2011/0250585 A1 | 10/2011 | Ingber et al. |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |
| 2012/0211373 A1 | 8/2012 | El-Sayed et al. |
| 2013/0137130 A1 | 5/2013 | Wells et al. |
| 2013/0224857 A1 | 8/2013 | Blak et al. |
| 2013/0280802 A1* | 10/2013 | Schulz ................ C12N 5/0606 435/363 |
| 2013/0288969 A1* | 10/2013 | Scadden ............. C12N 5/0647 514/11.8 |
| 2014/0038279 A1 | 2/2014 | Ingber et al. |
| 2014/0065660 A1 | 3/2014 | Hanseup et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2014/0342445 A1 | 11/2014 | Ingber et al. |
| 2015/0017674 A1 | 1/2015 | Christensen et al. |
| 2015/0023928 A1* | 1/2015 | Hassiotou .............. A61K 35/20 424/93.7 |
| 2015/0037320 A1 | 2/2015 | McGrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0252328 A1 | 9/2015 | Woodruff et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0145642 A1 | 5/2016 | Cui et al. |
| 2016/0152950 A1 | 6/2016 | Zhang et al. |
| 2016/0175401 A1* | 6/2016 | Spiegelman ....... G01N 33/6893 435/7.1 |
| 2017/0107498 A1 | 4/2017 | Sareen et al. |
| 2017/0226478 A1 | 8/2017 | Kerns et al. |
| 2017/0240866 A1 | 8/2017 | Wells et al. |
| 2017/0253856 A1 | 9/2017 | Douvaras et al. |
| 2017/0283772 A1 | 10/2017 | Qian et al. |
| 2017/0292116 A1 | 10/2017 | Wells et al. |
| 2017/0313976 A1 | 11/2017 | Kuwahara et al. |
| 2018/0021383 A1 | 1/2018 | George et al. |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0032215 A1 | 1/2020 | Svendsen et al. |
| 2020/0071673 A1 | 3/2020 | Sareen et al. |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0024886 A1 | 1/2021 | Laperle et al. |
| 2021/0033628 A1 | 2/2021 | Laperle et al. |
| 2021/0130774 A1 | 5/2021 | Sances et al. |
| 2023/0159896 A1 | 5/2023 | Sharma et al. |

FOREIGN PATENT DOCUMENTS

| | | | |
|---|---|---|---|
| AU | 2017213795 A1 | 8/2018 | |
| AU | 2017214468 A1 | 9/2018 | |
| AU | 2017319168 A1 | 3/2019 | |
| AU | 2017321489 A1 | 3/2019 | |
| AU | 2018235950 A1 | 10/2019 | |
| AU | 2018236273 A1 | 10/2019 | |
| AU | 2018270270 A1 | 12/2019 | |
| AU | 2017319168 B2 | 4/2021 | |
| AU | 2016341880 B2 | 5/2021 | |
| CA | 3002399 A1 | 4/2017 | |
| CA | 3013337 A1 | 8/2017 | |
| CA | 3013357 A1 | 8/2017 | |
| CA | 3034614 A1 | 3/2018 | |
| CA | 3035058 A1 | 3/2018 | |
| CA | 3055992 A1 | 9/2018 | |
| CA | 3056089 A1 | 9/2018 | |
| CA | 3064086 A1 | 11/2018 | |
| EP | 3008168 A1 | 4/2016 | |
| EP | 3031908 A1 | 6/2016 | |
| EP | 3365424 | 8/2018 | |
| EP | 3411470 A2 | 12/2018 | |
| EP | 3411472 A1 | 12/2018 | |
| EP | 3503901 A1 | 7/2019 | |
| EP | 3504319 A1 | 7/2019 | |
| EP | 3625331 A1 | 3/2020 | |
| EP | 3768823 A1 | 1/2021 | |
| EP | 3775161 A1 | 2/2021 | |
| EP | 3787613 A1 | 3/2021 | |
| EP | 3787649 A1 | 3/2021 | |
| EP | 4048282 | 8/2022 | |
| GB | 2561312 A | 10/2018 | |
| GB | 2562406 A | 11/2018 | |
| GB | 2564582 A | 1/2019 | |
| GB | 2568446 A | 5/2019 | |
| GB | 2569058 A | 6/2019 | |
| GB | 2574988 A | 12/2019 | |
| GB | 2575574 A | 1/2020 | |
| GB | 2561312 B | 3/2021 | |
| GB | 2564582 B | 9/2021 | |
| HK | 1260726 B2 | 7/2021 | |
| JP | 2003-511346 | 9/2000 | |
| JP | 2014-171434 A | 9/2014 | |
| JP | 2015-504676 A | 2/2015 | |
| JP | 2018-533940 A | 11/2018 | |
| JP | 2019-506861 A | 3/2019 | |
| JP | 2021-520784 A | 8/2021 | |
| JP | 2021-523700 A | 9/2021 | |
| JP | 2021-523888 A | 9/2021 | |
| KR | 20180069882 A | 6/2018 | |
| KR | 10-2022-0084282 | 6/2022 | |
| SG | 11201803143Y A | 5/2018 | |
| SG | 11201901621V A | 3/2019 | |
| SG | 11201901628X A | 3/2019 | |
| SG | 11201908358P A | 10/2019 | |
| SG | 11201908359U A | 10/2019 | |
| WO | 2000053218 | 9/2000 | |
| WO | WO 2005/021720 A2 | 3/2005 | |
| WO | WO 2010/009307 A2 | 1/2010 | |
| WO | WO 2010/108005 A2 | 9/2010 | |
| WO | WO 2011/109440 A1 | 9/2011 | |
| WO | 2012/100084 A1 | 7/2012 | |
| WO | WO-2012100084 A1 * | 7/2012 | ........... C12N 5/0662 |
| WO | WO 2012/118799 A2 | 9/2012 | |
| WO | 2013/056216 A1 | 4/2013 | |
| WO | WO 2013/065763 A1 | 5/2013 | |
| WO | WO 2013/071282 A1 | 5/2013 | |
| WO | WO 2013/086486 A1 | 6/2013 | |
| WO | WO 2013/106677 A1 | 7/2013 | |
| WO | 2013/184193 A2 | 12/2013 | |
| WO | WO-2013184193 A2 * | 12/2013 | ......... G01N 33/5011 |
| WO | WO 2014/159356 A1 | 10/2014 | |
| WO | WO 2014/172682 A1 | 10/2014 | |
| WO | WO 2014/176606 A1 | 10/2014 | |
| WO | WO 2015/052143 A1 | 4/2015 | |
| WO | WO 2015/057261 A1 | 4/2015 | |
| WO | WO 2015/126528 A1 | 8/2015 | |
| WO | WO 2015/138032 A2 | 9/2015 | |

(56) References Cited

FOREIGN PATENT DOCUMENTS

| | | | |
|---|---|---|---|
| WO | WO 2015/138034 A2 | 9/2015 | |
| WO | WO 2015/143342 A1 | 9/2015 | |
| WO | WO 2015/153451 A1 | 10/2015 | |
| WO | WO 2015/163823 A1 | 10/2015 | |
| WO | WO 2015/181253 A1 | 12/2015 | |
| WO | WO 2015/183920 A2 | 12/2015 | |
| WO | WO 2015/188131 A1 | 12/2015 | |
| WO | WO 2016/061464 A1 | 4/2016 | |
| WO | WO 2016/063985 A1 | 4/2016 | |
| WO | WO 2016/086040 A1 | 6/2016 | |
| WO | WO 2016/093222 A1 | 6/2016 | |
| WO | 2016/141137 A1 | 9/2016 | |
| WO | WO-2016141137 A1 * | 9/2016 | ........... B29C 64/106 |
| WO | WO 2016/162747 A1 | 10/2016 | |
| WO | WO 2016/183252 A1 | 11/2016 | |
| WO | WO 2017/035119 A1 | 3/2017 | |
| WO | WO 2017/070224 A1 | 4/2017 | |
| WO | WO 2017/075271 A1 | 5/2017 | |
| WO | WO 2017/078807 A1 | 5/2017 | |
| WO | 2017/112455 A1 | 6/2017 | |
| WO | WO 2017/123806 A1 | 7/2017 | |
| WO | WO 2017/136462 A2 | 8/2017 | |
| WO | WO 2017/136479 A1 | 8/2017 | |
| WO | WO 2017/143049 A1 | 8/2017 | |
| WO | WO 2017/200486 A1 | 11/2017 | |
| WO | WO 2017/219000 A1 | 12/2017 | |
| WO | 2018/035214 A1 | 2/2018 | |
| WO | WO 2018/044885 A1 | 3/2018 | |
| WO | WO 2018/044934 A1 | 3/2018 | |
| WO | 2018/140647 A1 | 8/2018 | |
| WO | 2018/176001 A1 | 9/2018 | |
| WO | WO 2018/170139 A1 | 9/2018 | |
| WO | WO 2018/170180 A1 | 9/2018 | |
| WO | WO 2018/213773 A1 | 11/2018 | |
| WO | 2019/122291 A1 | 6/2019 | |
| WO | 2019/178550 A1 | 9/2019 | |
| WO | WO 2019/183597 A1 | 9/2019 | |
| WO | WO 2019/195798 A1 | 10/2019 | |
| WO | WO 2019/195800 A1 | 10/2019 | |
| WO | WO 2019/212690 A1 | 11/2019 | |
| WO | WO 2019/212691 A1 | 11/2019 | |
| WO | 2021/081229 A1 | 4/2021 | |
| WO | 2021/081237 A1 | 4/2021 | |
| WO | 2021222724 A1 | 11/2021 | |

OTHER PUBLICATIONS

Qu et al., ("Differentiation of Human Induced Pluripotent Stem Cells to Mammary-like Organoids," Stem Cell Reports vol. 8 , 1-11, Feb. 14, 2017).*
Gurusamy et al ("Hepatocyte growth factor-like protein is a positive regulator of early mammary gland ductal morphogenesis," Mechanisms of Development 133 (2014) 11-22).*
Zhang et al ("FGF ligands of the postnatal mammary stroma regulate distinct aspects of epithelial morphogenesis," Development (2014) 141, 3352-3362).*
Simeone et al ("The OTX family," Current Opinion in Genetics & Development2002, 12:409-415).*
Arendt et al ("Form and Function: how Estrogen and Progesterone Regulate the Mammary Epithelial Hierarchy;" J Mammary Gland Biol Neoplasia (2015) 20:9-25) (Year: 2015).*
Qiao et al ("AP2γ regulates neural and epidermal development downstream of the BMP pathway at early stages of ectodermal patterning;" Cell Research (2012) 22:1546-1561) (Year: 2012).*
Lin et al ("Embryoid body formation from human pluripotent stem cells in chemically defined E8 media;" StemBook, ed. (Jun. 1, 2014) (Year: 2014).*
ISR and Written Opinion for PCT/US2018/015318 dated May 2, 2018, 16 pages.
Hens et al., BMP4 and PTHrP interact to stimulate ductal outgrowth during embryonic mammary development and to inhibit hair follicle induction, Development, 2007, 134:1221-1230.

Farrelly et al., Extracellular matrix regulates apoptosis in mammary epithelium through a control on insulin signaling, The Journal of Cell Biology, 1999, 144(6):1337-1347.
Qu et al., Differentiation of human induced pluripotent stem cells to mammary-like organoids, Stem Cell Reports, 2017, 8(2):205-215.
International Search Report and Written Opinion for PCT/US2018/024198 dated Aug. 13, 2018, 15 pages.
International Search Report and Written Opinion for PCT/US2020/056896 dated Oct. 22, 2020, 11 pages.
International Search Report and Written Opinion for PCT/US2020/056906 dated Mar. 16, 2021, 13 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLoS One, 2014, 9(1), 14 pages.
Badger et al., Parkinson's disease in a dish – Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Ichida et al., Probing disorders of the nervous system using reprogramming approaches, The EMBO Journal / European Molecular Biology Organization, 2015, vol. 34, No. 11, pp. 1456-1477.
Kessler et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. Plos One 9(3): e92427. p. 1-9 (Year: 2014).
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Levanon, et al., Primary ex vivo cultures of human fallopian tube epithelium as a model for serous ovarian carcinogenesis, Oncogene, 2010, 29(8): 1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells

(56) References Cited

OTHER PUBLICATIONS in threedimensional culture with radial flow bioreactor. Regenerative Therapy 2 (2015) 24-31 (Year: 2015).
O'Neill et al., Genetic disorders coupled to ROS deficiency, Redox Biology, 6: 135-156. (Year: 2015).
Rey, et al., Chapter 7, Sexual Differentiation, 2016 [online]. [Retrieved on Sep. 19, 2019]. Retrieved from the Internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCI [alpha] Trans, Cell, Elsevier,2013, vol. 155, No. 6, pp. 1351-1364.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Sun et al., Role of Bone Morphogenetic Protein-2 in Osteogenic Differentiation of MesenChymal Stem Cells, Molecular Medicine Reports, 2015, vol. 12, pp. 4230-4237.
Vogel et al., Co-culture of human induced pluripotent stem cells 9iPSCs) with human fallopian tube epithelium (FTE) Induces Pax8 and CK7 expression: Initial steps in modeling fallopian tube epithelium to study serous carcinogenesis; Gynecologic Oncology, 2015 137(1):206.
Zhang et al., Regulation and Patterning of Cell Differentiation and Pluripotency, Thesis, Columbia University, pp. 1-177, 2011.
Zhou et al., Rapid and efficient generation of transgene-free iPSC from a small volume of cryopreserved blood, Stem Cell Reviews and Reports 11: 652-665. (Year: 2015).
International Search Report and Written Opinion of PCT/US2017/013250 dated Mar. 31, 2017, 12 Pages.
International Search Report and Written Opinion of PCT/US2016/057724 dated Jan. 9, 2017, 17 Pages.
International Search Report and Written Opinion of PCT/US2017/016098 dated Jun. 22, 2017, 14 Pages.
International Search Report and Written Opinion of PCT/US2017/016079 dated Jul. 25, 2017, 26 Pages.
International Search Report and Written Opinion of PCT/US2017/049193 dated Nov. 6, 2017, 9 Pages.
International Search Report and Written Opinion of PCT/US2017/049115 dated Nov. 28, 2017, 11 Pages.
International Search Report and Written Opinion of PCT/US2018/022511 dated Jul. 26, 2018, 11 Pages.
International Search Report and Written Opinion of PCT/US2018/033498 dated Aug. 9, 2018, 9 Pages.
International Search Report and Written Opinion for PCT/US2018/022455 dated Aug. 23, 2018, 13 pages.
International Search Report and Written Opinion of PCT/US2019/026193 dated Jan. 7, 2019, 8 pages.
International Search Report and Written Opinion of PCT/US2019/026178 dated Jun. 11, 2019, 14 Pages.
International Search Report and Written Opinion of PCT/US2019/026183 dated Jun. 12, 2019, 10 Pages.
International Search Report and Written Opinion of PCT/US2019/026195 dated Jun. 12, 2019, 10 pages.
International Search Report and Written Opinion of PCT/US2019/023749 dated Jun. 25, 2019, 12 Pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511, dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
EP 19782199.4 Partial Supplementary Search Report dated Nov. 30, 2021, 15 pages.
EP 19796470.3 European Extended Search Report dated Dec. 10, 2021, 11 pages.
EP 19771249.0 Partial Supplemental European Search Report dated Nov. 8, 2011, 15 pages.
EP 18802136.4 Examination Report dated Oct. 14, 2021, 8 pages.
EP 18802136.4 Extended European Search Report dated Jan. 22, 2021, 12 pages.
GB1811716.8 Examination Report dated Feb. 12, 2020, 6 pages.
GB 1903007.1 Search Report dated Apr. 1, 2019, 8 pages.
GB 1903007.1 Search Report dated Jun. 24, 2020, 3 pages.
JP 2018-540028 Notice of Reasons for Rejection dated Mar. 1, 2021.
SG 11201803143Y Search Report dated Jul. 15, 2019, 3 pages.
SG 11201901628X Written Opinion dated Mar. 10, 2021, 9 pages.
Abbott et al., Structure and function of the blood-brain barrier, Neurobiology of Desease, 2010 27:13-25.
Abbott et al., Structure and function of the blood-brain barrier, Pharm Tox BBB: 1-3, Feb. 2010, Conf. Abstract.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brittan et al., The gastrointestial stem cell, Cell Prolif., 2004, vol. 37, pp. 35-53.
Brown et al., Recreating Blood-Brain Barrier Physiology and Structure on Chip: A Novel Neurovascular Microfluidic Bioreactor, 2015, Biomicrofluidics, vol. 9(5).

(56) References Cited

OTHER PUBLICATIONS

Burkhardt et al., A Cellular Model for Sporadic ALS using Patient-Derived Induced Pluripotent Stem Cells, Molecular and Cellular Neuroscience, 2013, vol. 56, pp. 355-364.

Cashman et al., Induced Pluripotent Stem Cells and Motor Neuron Disease: Toward an Era of Individualized Medicine, J. Neurosci, 2013, vol. 33, pp. 8587-8589.

Chal et al., Differentiation of Pluripotent Stem Cells to Muscle Fiber to Model Duchenne Muscular Dystrophy, 2015, Nature Biotechnology, vol. 33(9), pp. 962-969.

Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.

Chou et al., Efficient human iPS cell derivation by a non-integrating plasmid from blood cells with unique epigenetic and gene expression signatures, Cell Research, 2011, 21:3, pp. 518-529.

Danmark et al., Development of a novel microfluidic device for long-term in situ monitoring of live cells in 3-dimensional matrices, Biomed Microdevices, 2012, pp. 885-893.

Date et al., Mini-Gut Organoids: Reconstruction of the Stem Cell Niche, Annu. Rev. Cell Dev. Biol., 2015, vol. 31, pp. 269-289.

Demers et al., Development-on-Chip: in vitro Neutral Tube Patterning with a Microfluidic Device, Development, 2016, vol. 143(11), pp. 1884-1892.

Dhumpa et al., Temporal Gradients in Microfluidic Systems to Probe Cellular Dynamics: A Review, Anal. Chim. Acta, 2012, vol. 743, pp. 9-18.

Dimos et al., Induced Pluripotent Stem Cells Generated from Patients with ALS can be Differentiated into Motor Nuerons, Science, 2008, vol. 321, pp. 1218-1221.

Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.

Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.

Esch et al., Organs-on-Chips at the Frontiers of Drig Discovery, Nature Reviews, 2015, vol. 14(4), pp. 248-269.

Evans et al., The Development of a Method for the Preparation of Rat Intestinal Epithelial Cell Primary Cultures, 1992, Journal of Cell Science, vol. 101, pp. 219-231.

Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.

Fridley et al., Hydrodynamic modulation of pluripotent stem cells, Stem cell research & therapy, 2012, vol. 45.

Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.

Gel, Wikipedia, pp. 1-29 Downloaded on Sep. 14, 2018, https://en.wikipedia.org/wiki/Gel.

Gracz et al., CD24 and CD44 Mark Human Intestinal Epithelial Cell Populations with Characteristics of Active and Facultative Stem Cells, 2013, Stem Cells, vol. 31(9), pp. 2024-2030.

Gross et al., Applications of Microfluidics for Neuronal Studies, 2007, Journal of the Neurological Sciences, vol. 252, pp. 135-143.

Hu et al. Neural differentiation of human induced pluripotent stem cells follows developmental principles but with variable potency, PNAS, 2010, vol. 107(9), pp. 4335-4340.

Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.

Hughes et al., Matrigel: A Complex Protein Mixture Required for Optimal Growth of Cell Culture, 2010, Proteomics, vol. 10, pp. 1886-1890.

Huh et al., From 3D Cell Culture to Organs-on-Chips, Trends in Cell Biology, 2011, vol. 21(2), pp. 745-754.

Huh et al., Microfabrication of Human Organs-on-Chips, Nature Protocols, 2013, vol. 8(11), pp. 2135-2157.

Hynds et al., Concise Review: The Relevance of Human Stem Cell-Derived Organoid Models for Epithelial Transitional Medicine, Stem Cells, 2013, vol. 1 31, pp. 417-422.

Jang et al., JAK-STAT Pathway and Myogenic Differentiation, JAKSTAT, 2013, vol. 2(2), Pages e23282-1 to e-23282-6.

Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.

Jenke et al., DNA Methylation Analysis in the Intestinal Epithelium—Effect of Cell Separation on Gene Expression an Methylation Profile, PLOS One, 2013, vol. 8(2), pp. 1-8.

Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.

Kauffman et al., Alternative functional in vitro models of human intestinal epithelia, frontiers in Pharmacology, Jul. 2013, vol. 4, Article 79, 18 pages.

Kelamangalath et al. k-Opioid receptor inhibition of calcium oscillations in spinal cord neurons,, Molecular Pharmacology, 2011, 79:1061-1071.

Kilic et al., Brain-on-a-Chip Model Enables Analysis of Human Neuronal Differentiation and Chemotaxis, 2016, Lab on a Chip, vol. 16(21), pp. 4152-4162.

Kilpatrick, K. et al., Genetic and chemical activation of TFEB mediates clearance of aggregated a-synuclein, PLoS One, 2015, 10:3, pp. 1-21.

Kim et al., Human Gut-on-a-Chip Inhabited by a Microbial Flora that Experiences Intestinal Peristalsis-Like Motions and Flow, Lab on a Chip, 2012, vol. 12(12). pp. 2165.

Kim et al., Gut-on-a-Chip Microenvironmental Induces Human Intestinal Cells to Undergo Villus Differentiation, Integrative Biology, 2013, vol. 5(9), p. 1130-1140.

Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.

Kirkby et al., A Role for Correlated Spontaneous Activity in the Assembly of Neural Circuits, 2013, Neuron, vol. 80(5), 27 Pages.

Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.

Kondo et al., Ipsc-based Coound screening and in vitro trials identify a synergistic anti-amyloid b combination for Alzheimer's Disease, Cell Reports, 2017, vol. 21, pp. 2304-2312.

Kuratnik et al., Intestinal organoids at tissue surrogates for toxicological and pharmacological studies, biochemical Pharmacology, Apr. 25, 2013, vol. 85:12, pp. 1721-1726.

Kwasny et al., Static biofilm cultures of gram-positive pathogens grown in a microtiter format used for anti-biofilm drug discovery, Current Protocols in Pharmacology, 2010, 13A.8.1-13A.8.23.

Lee et al. Microfluidic 3D bone tissue model for high-throughput evaluation of would healing and infection-preventing biomaterials, Biomaterials 33.4 2012 999-1006.

Lenner, J., Fat Cells More Easily Programmed into iPS Cells, 2009, pp. 1-2.

Lenzi et al., Differentiation of Control and ALS Mutant Human iPSCs into Functional SkeletalMuscle Cells, A Tool for the Study of Neuromuscolar Diseases, Stem Cell Research, 2016, vol. 17, pp. 140-147.

Li et al., Protein kinase C controls lysosome biogenesis independently of mTORC1, Nature Cell Biology, 2016, 10:10, pp. 1-26.

Lin et al., Neural Stem Cell Differentiation in a Cell-Collagen-Bioreactor Culture System, 2004, Developmental Brain Research, vol. 153, pp. 163-173.

Lippmann, et al., Human Blood-Brain Barrier Endothelial Cells Derived from Pluripotent Stem Cells, 2012, Nature Biotechnology, vol. 30(8), pp. 783-791.

(56) References Cited

OTHER PUBLICATIONS

Lippmann et al., A Retinoic Acid-Enhanced, Multicellular Human Blood-Brain Barrier Model Derived from Stem Cell Sources, Scientific Reports, vol. 4(1), 2014, pp. 1-10.

Lippmann et al., Chemically Defined Differentiation of Human Pluripotent Stem Cells to Hindbrain and Spinal Cord Neural Stem Cells with Defined Regional Identifies, 2015, Protocol Exchange.

Loo et al., An Arduous Journey from Human Pluripotent Stem Cells to Functional Pancreatic Beta Cells, Diabetes Obes Metab., 2018, vol. 20(3), pp. 3-13.

Martin et al., Laparoscopic Colorectal Resection in the Obese Patient, 2011, Clinics in Colon and Rectal Surgery, vol. 24(4), pp. 263-273.

Massumi et al., Efficient Programming of Human Eye Conjunctiva-Derived Induced PluripotentStem (ECiPS) Cells into Definitive Endoderm-Like Cells, Experimental Cell Research, 2014, vol. 322, pp. 51-61.

Mcgaugh et al., Efficient Differentiation of Pluripotent Stem Cells to NKX6-1 + Pancreating Progenitors, Journal of Visualized Experiments, 2017, vol. 121, pp. 1-5.

Mckinney, C.E. et al., Using induced pluripotent stem cells derived neurons to model brain diseases, Neural Regeneration Research, 2017, 12:7 pp. 1-11.

Murphy et al., Scaffolds for 3D in vitro Culture of Neural Lineage Cells, Acta Biomaterialia, 2017, vol. 54, pp. 1-20.

Myotube, Medical Dictionary—Downloaded on Jul. 8, 2018, https://medical-dictionary.thefreedictionary.com/myotube, p. 1.

Naik et al., In vitro blood-brain models: Current and perspective technologies, J. Phar Sci., 2012, 1014(4):1337-1354.

Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.

Niego et al., Improved Method for the Preparation of a Human Cell-based, Contact Model of the Blood-Brain Barrier, 2013, J. Vis. Exp., vol. 81(e50934), pp. 1-9.

Nostro et al., Efficient Generation of NKX6-1+ Pancreatic Progenitors from Multiple Human Pluripotent Stem Cell Lines, Stem Cell Reports, 2015 4(4), pp. 591-604.

Ochetta et al., High-Throughput Microfluidic Platform for 3D Cultures of Mesenchymal StemCells, Towards Engineering Developmental Processes, Scientific Reports, 2015, vol. 5, Article No. 10288, pp. 1-12.

Okita et al., A More Efficient Method to Generate Integration-Free Human iPS Cells, 2011, Nature Methods, vol. 8(5), pp. 409-412.

Ong et al., A Gel-Free 3D Microfluidic Cell Culture System, Biomaterials, 2008, vol. 29, pp. 3237-3244.

Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.

Perry et al., The Neuromuscular junction: Structure and function, downloaded from the internet (Neuromuscular junction: Parts, structure and steps/Kenhub>, pp. 1-6, downloaded Feb. 25, 2021.

Polini et al., Organs-on-a-Chip: A New Tool for Drug Discovery, Expert Opinion on Drug Discovery, 2014, vol. 9(4), pp. 335-352.

Polydimethylsiloxane—Wikipedia, dowloaded on Feb. 24, 2021 <Silicon dioxide—Wikipedia>, pp. 1-11.

Prabhakarpandian et al., SyM-BBB: A Microfluidic Blood Brain Barrier Model, Lab on a Chip, 2013, vol. 13(6), p. 1093.

Qian et al., A Simple and Efficient System for Regulating Gene Expression in Human Pluripotent Stem Cells and Derivatives, Stem Cells, 2014, vol. 32(5), pp. 1230-1238.

Rajesh et al., Human Lymphoblastoid B-Cell Lines Reprogrammed to EBV-FREE Induced Pluripotent Stem Cells, 2011, Blood, vol. 118(7), pp. 1797-1800.

Rhee et al., Patterned Cell Culture Inside Microfluidic Devices, Lab Chip, 2005, vol. 5(1), pp. 102-107.

Roberts et al., Expression of the Thyroid Hormone Transports Monocarboxylate Transporter-8(SLC16A2) and Organic Ion Transporter-14 (SLCO1C1) at the Blood-Brain Barrier, Endocrinol, 2008, vol. 149(12), pp. 6251-6261.

Rosenberg et al., Calcium Signaling in Neuronal Development, 2011, Cold Spring Harb Perspect Biol., vol. 3(a004259), 13 Pages.

Ryan et al., Progranulin is expressed within motor neurons and promotes neuronal cell survival, BMC Neuroscience, 2009, 10:130, pp. 1-22.

Sances et al., Modeling ALS with Motor Neurons Derived from Human Induced Pluripotent Stem Cells, Nature Neuroscience, 2016, vol. 19, pp. 542-553.

Santaguida et al., Side By Side Comparison Between Dynamic Versus Static Models of Blood-Brain-Barrier in vitro: A Permeability Study, Brain Research, 2006, vol. 1109(1), pp. 1-13.

Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.

Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.

Schiesser et al., Derivation of Insulin-Producing Beta-Cells from Human Pluripotent Stem Cells, The Review of Diabetic Studies, 2014, vol. 11(1), pp. 6-18.

Schwartz et al., Allan-Herndon-Dudley Syndrome and the Monocarboxylate Transporter 8 (MCT8) Gene, 2005, AJHG, vol. 77(1), pp. 41-53.

Shimuzu et al., Microfluidic Devices for Construction of Contractile Skeletal Muscle Microtissues, J. Biosci. Bioeng., 2015, vol. 119, pp. 212-216.

Shimojo et al., Rapid, Efficient and Simple Motor Neuron Differentiation from Human Pluripotent Stem Cells, Molecular Brain, 2015, vol. 8(1), pp. 1-15.

Silicon dioxide—Wikipedia, downloaded on Feb. 24, 2021 <silicon dioxide—Wikipedia> pp. 1-20.

Soria-Valles et al., NF-kB Activation Impairs Somatic Cell Reprogramming in Ageing, 2015, Nat. Cell Biol., vol. 17(8), pp. 1004-1013.

Southam et al., Microfluidic primary culture model of the lower motor neuron-neuromuscular junction circuit, J Neurosc Meth 2013, 218:164-169.

Southam et al., A Novel in vitro Primary Culture Model of the Lower Motor Neuron-Nueromuscular Junction Circuit, Microfludic and Compartmentalized Platforms for Neurobiological Research, Humana Press, 2015, pp. 181-193, abstract only.

Stepniewski et al., Induced Pluripotent Stem Cells as a Model for Diabetes Investigation, Scientific Reports, 2015, 5:8597, 14 pages.

Sundberg et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.

Telias et al., Electrical Maturation of Neurons Derived from Human Embryonic Stem Cells, F1000 Research, 2014, vol. 3(196), p. 1-12.

Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.

Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.

Uzel et al., New Microfluidic Chip Replicates Muscle-Nerve Connection, 2016, Science Daily, pp. 1-4.

Uzel et al., Microfluidic Device for the Formation of Optically Excitable, Three-Dimensional, Compartmentalized Motor Units, Science Advances, 2016, pp. e1501429.

Vatine et al., Human iPSC-Derived Blood-Brain Barrier Chips Enable Disease Modeling and Personalized Medicine Applications, Cell Stem Cell, 2019, vol. 24(6), pp. 995-1005.

Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.

(56) References Cited

OTHER PUBLICATIONS

Wang et al., Microfluidics: A new cosset for neurobiology, Lab Chip, 2009, 9:644-652.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Wu et al., Nuclear Accumulation of Histone Deacetylase 4 (HDAC4) Exerts Neurotoxicity in Models of Parkinson's Disease, Mol Neurobiol, 2017, vol. 54, pp. 6970-6983.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Yang et al., From the vascular microenvironment to neurogenesis, Brain Res Bull. Jan. 15, 2011; 84(1):1-7.
Yu et al., A Microfluidic-Based Multi-Shear Device for Investigating the Effects of Low Fluid-Induced Stresses on Osteoblasts, PLOS One, 2014, vol. 9(2), pp. 1-7.
Zhang et al., Patient-specific 3D microfluidic tissue model for multiple myeloma, Tissue Engineering Part C: Methods, 2014, pp. 663-670.
Zilio et al., Universal Hydrophilic Coating of Thermoplastic Polymers Currently Used in Microfluidics, 2014, Biomed. Microdevices, vol. 16(1), pp. 107-114.
Ionescu et al., Compartmental microfluidic system for studying muscle-neuron communication and neuromuscular junction maintenance, 2016 European Journal of Cell Biology, 95:69-88.
DMEM F-12 Formulation, pp. 1-5, 2022.
Mehta et al., The actions of retinoids on cellular growth correlate with their actions on gap junctional communication, JCB 108, 1053-1065, 1989.
Essential 8 medium C037161 Essential8System Brochure (thermofisher.com), downloaded on Aug. 24, 2022, pp. 1-2.
ISR and WO for PCT/US2021/030128 dated Aug. 25, 2021, 10 pages.
JP Reasons for Rejection—2020-560893 dated Feb. 6, 2023, 9 pages.
Matsumoto et al., Functional neurons generated from T Cell-derived induced pluripotent stem cells for neurological disease modeling, 2016, 6:422-435.
Moors et al., Therapeutic potential of autophagy-enhancing agents in Parkinson's disease, Molecular Neurodegeneration, 2017, 12:11, p. 1-18.
Okita et al., An efficient nonviral method to generate integration-free human-induced pluripotent stem cells from cord blood and peripheral blood cells, Stem Cells 2013, 31:458-466.
Kondo et al., iPSC-Based compound screening and in vitro trials identify a synergistic anti-amyloid B combination for Alzheimer's Disease, Cell Reports 2017, 21:2304-2312.
Hojo et al., Development of high-throughput screening system for osteogenic drugs using a cell-based sensor, Biochemical and Biophysical Research Communiatins 376(2):375-379, 2008.
Munera et al., Differentiation of Human Pluripotent Stem Cells into Colonic Organoids via Transient Activation of BMP Signaling, Cell Stem Cell, 21, 51-64, 2017.
Kim, et al. [3-Cell regeneration through the transdifferentiation of pancreatic cells: Pancreatic progenitor cells in the pancreas, Journal of Diabetes Investigation 7(3): 286-296. doi: 10.1111/jdi .12475. (Year: 2016).
Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/ j.ijcard.2015.06.038. (Year: 2015).
Hayes et al., Strategies to generate induced pluripotentstem cells, Methods in Molecular Biology 1029: 77-92. doi: 10.1007/978-1-62703-478-4_6 (Year: 2013).
Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.

\* cited by examiner

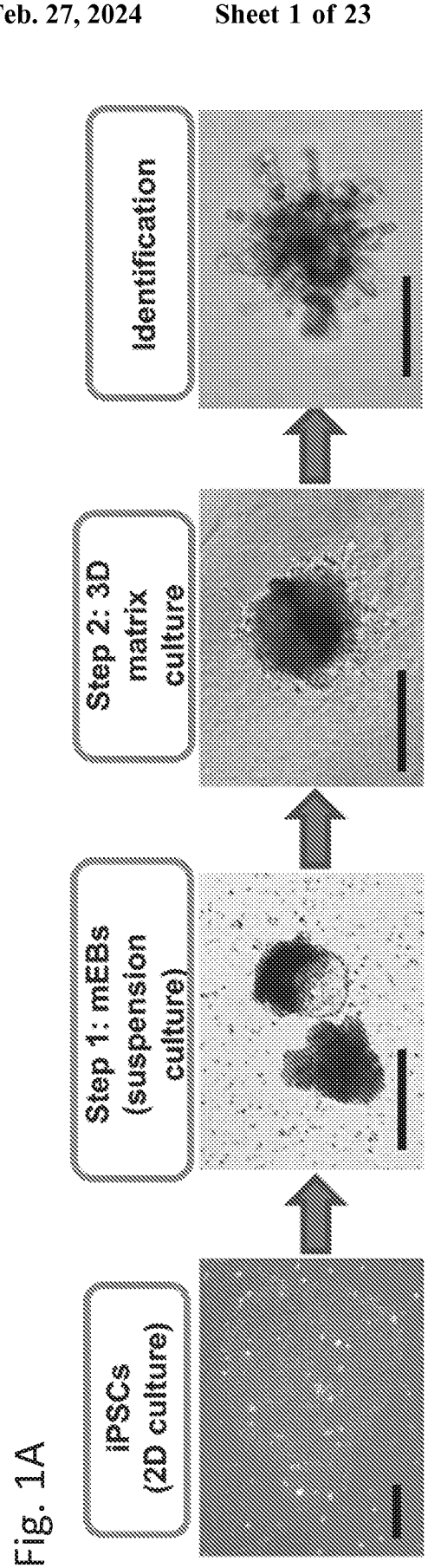

FIG. 2A
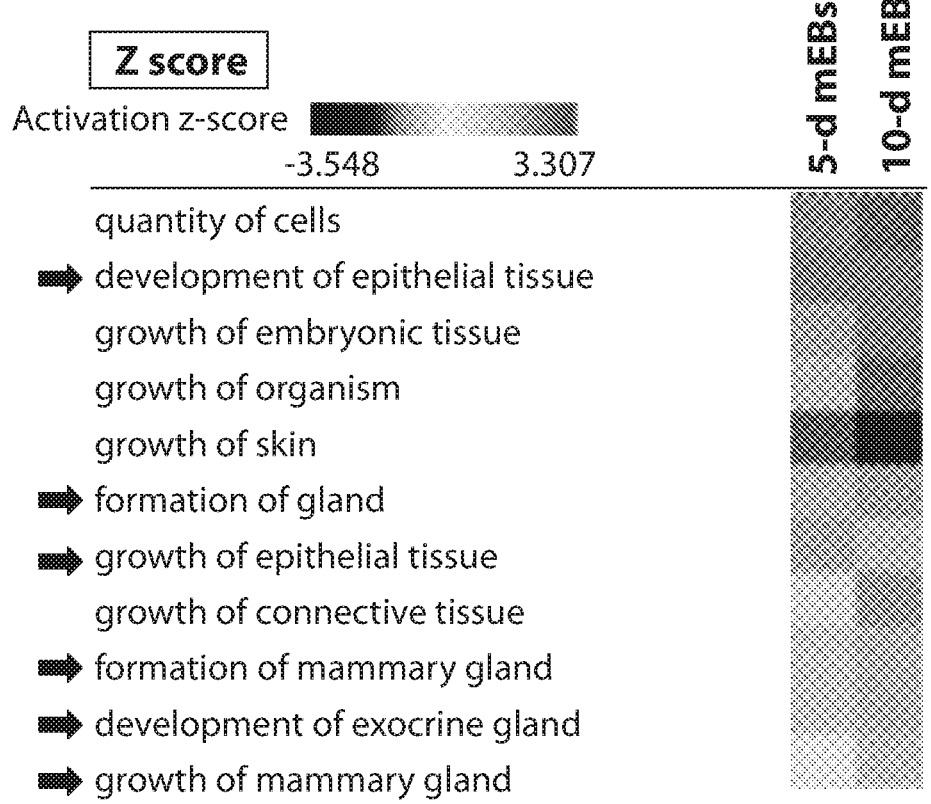
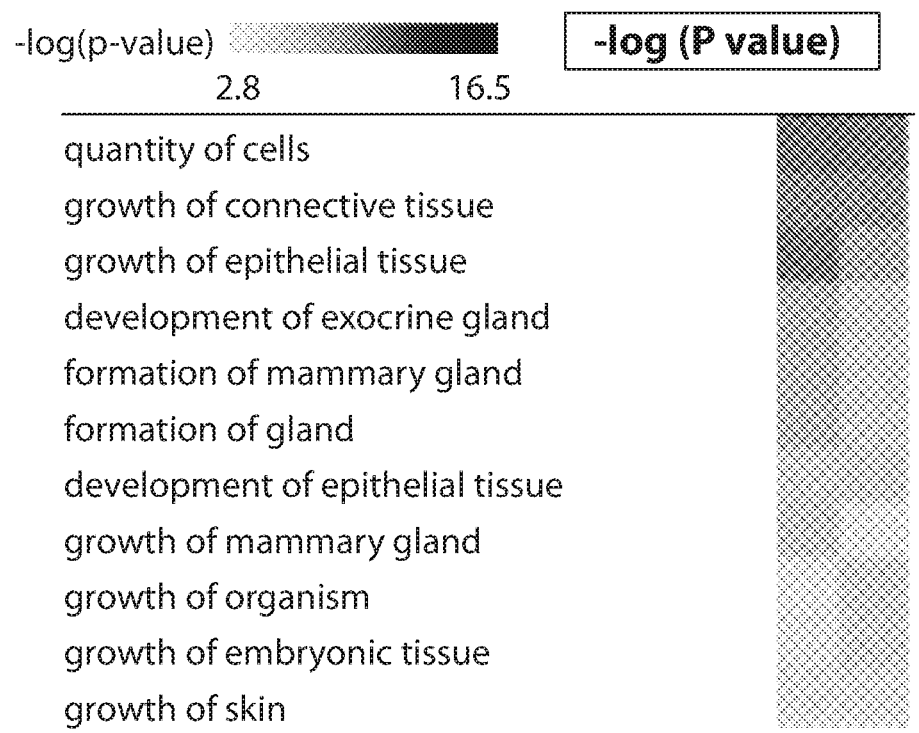

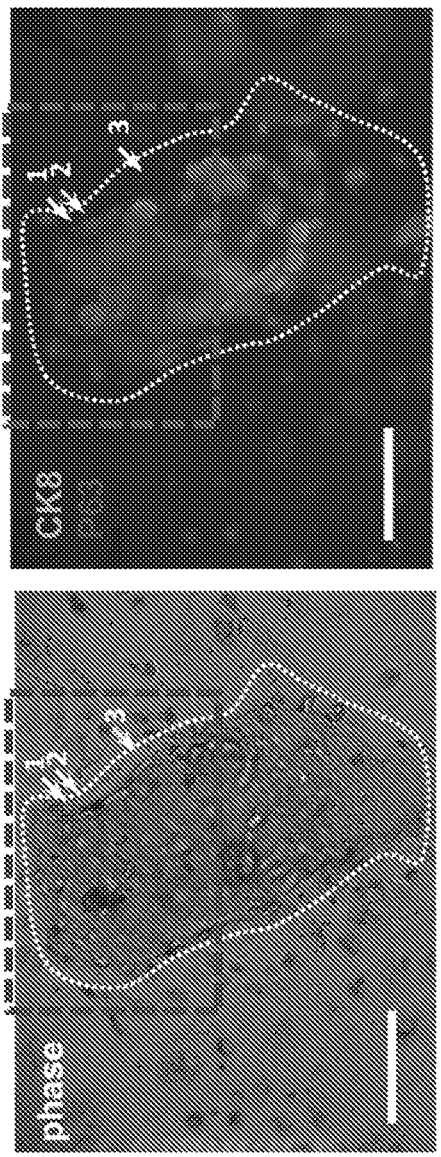
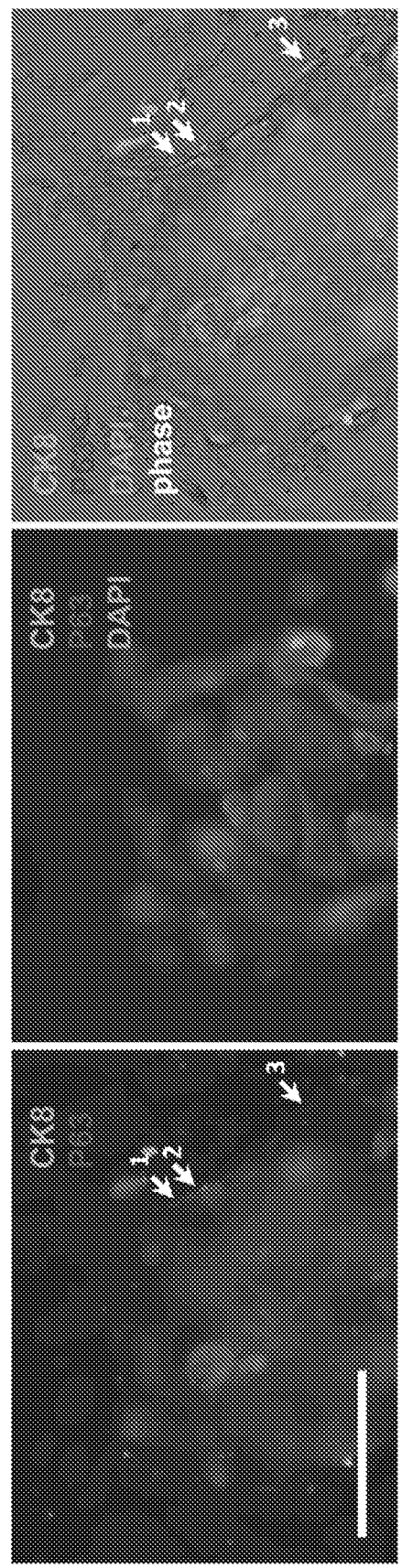
Fig. 4A
Fig. 4B

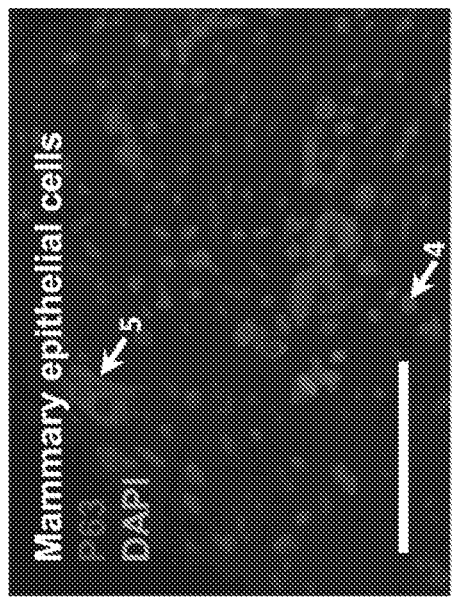
Fig. 4D
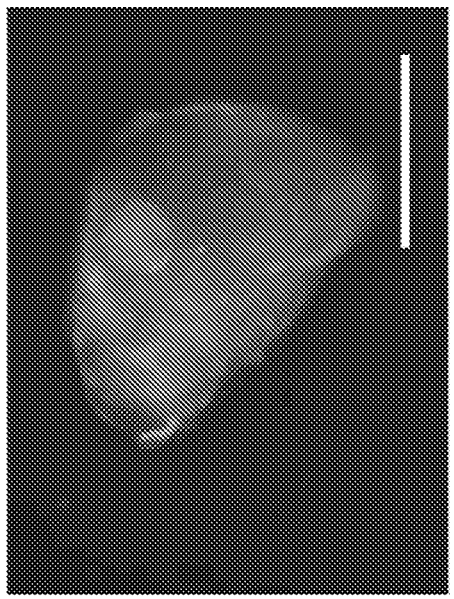
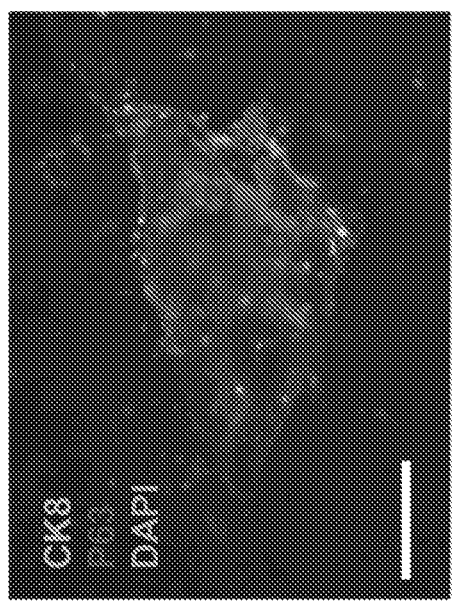
Fig. 4C
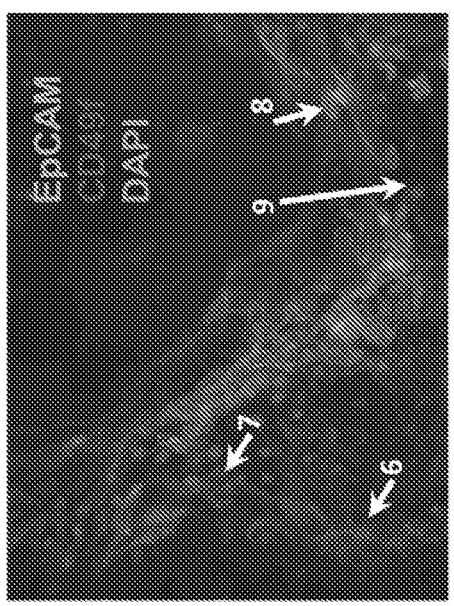
Fig. 4E

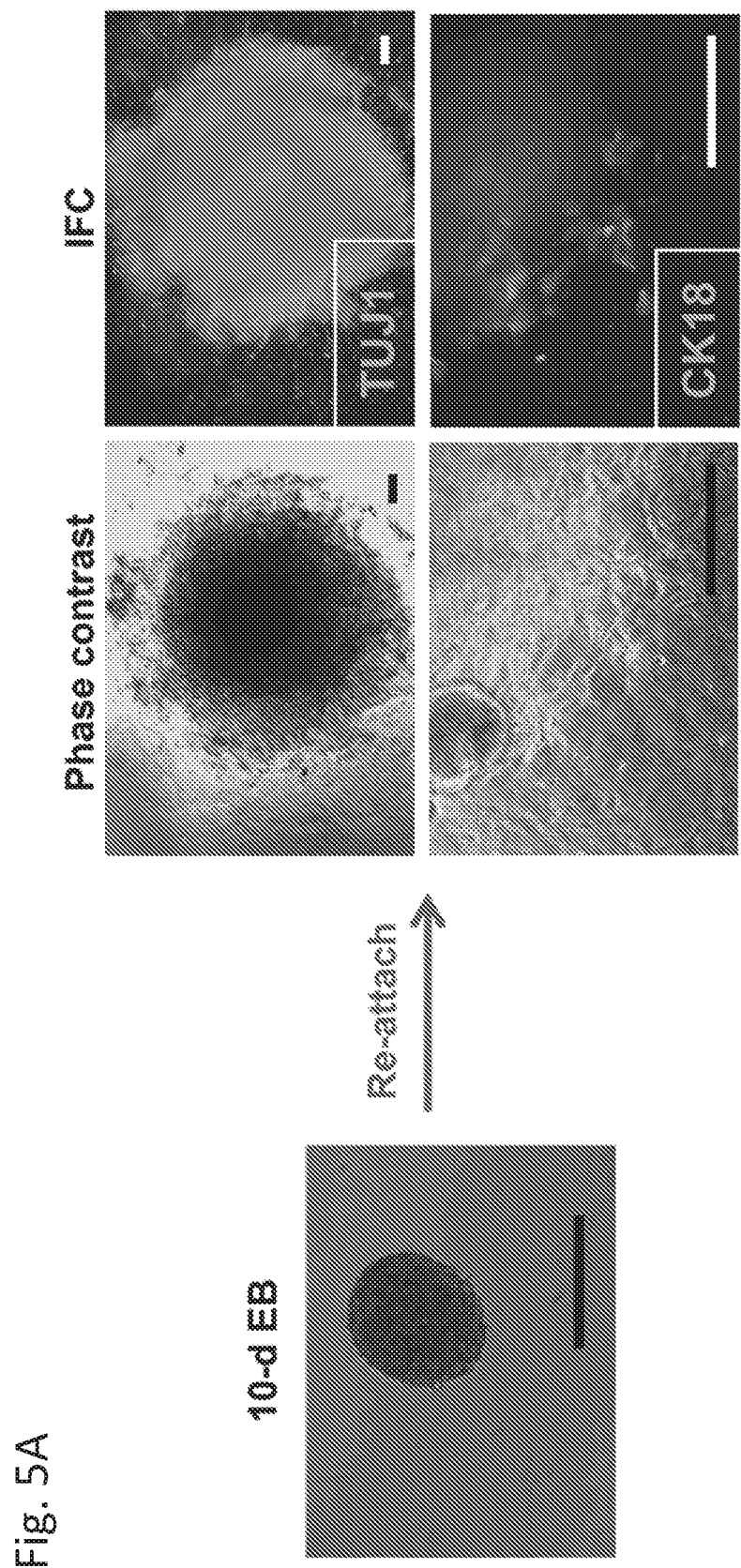

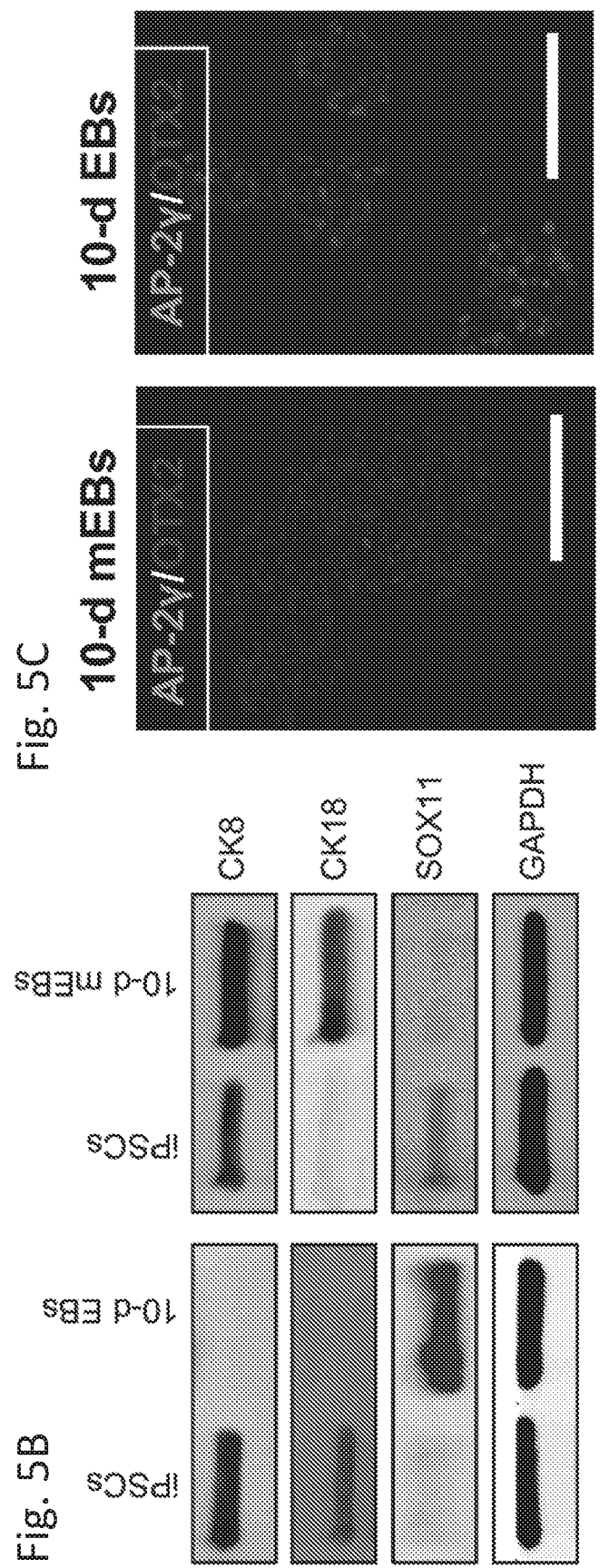

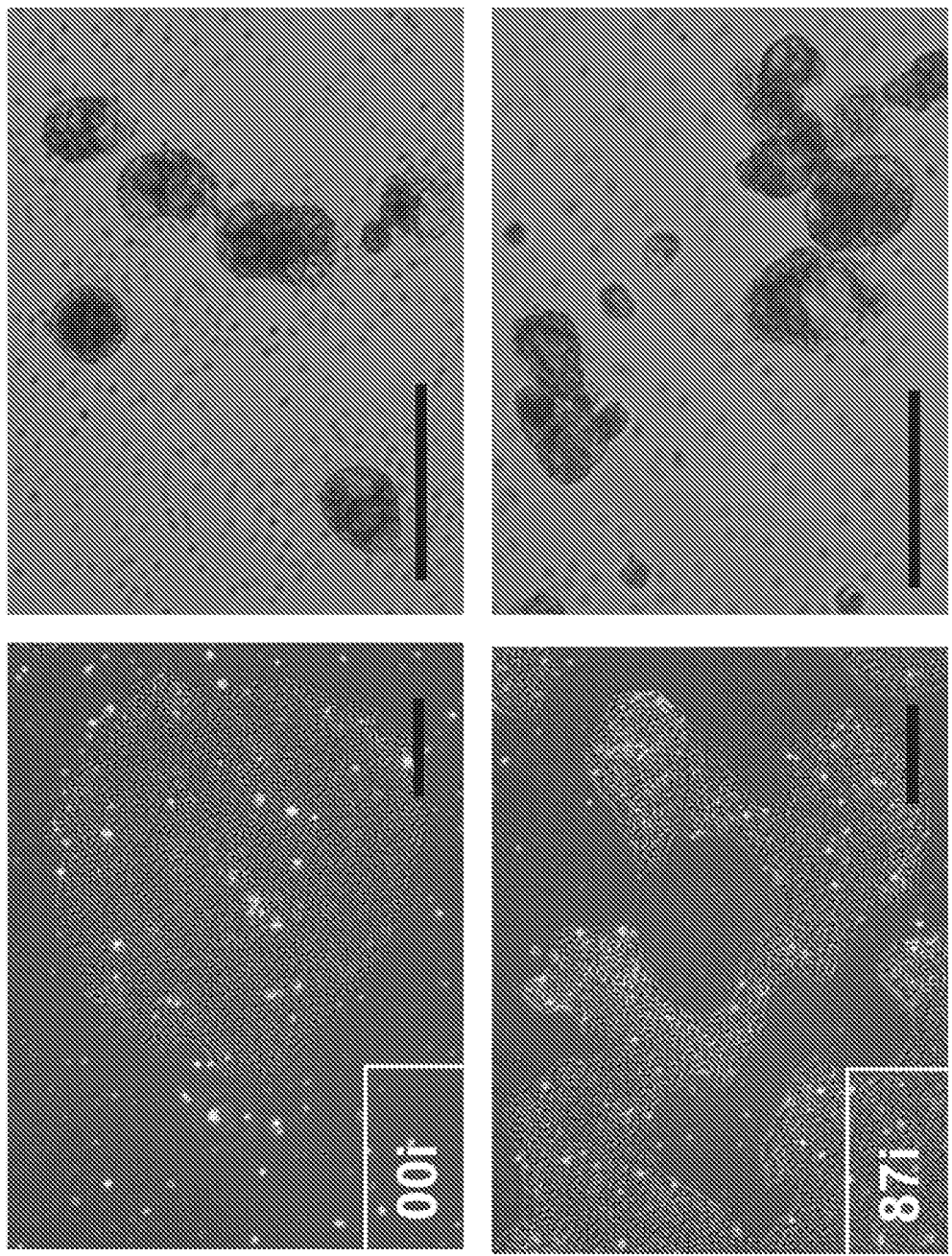

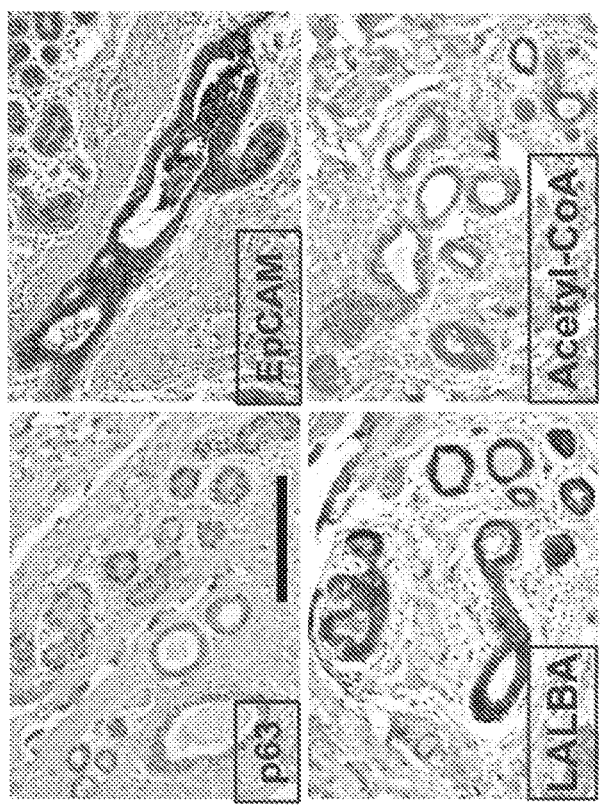
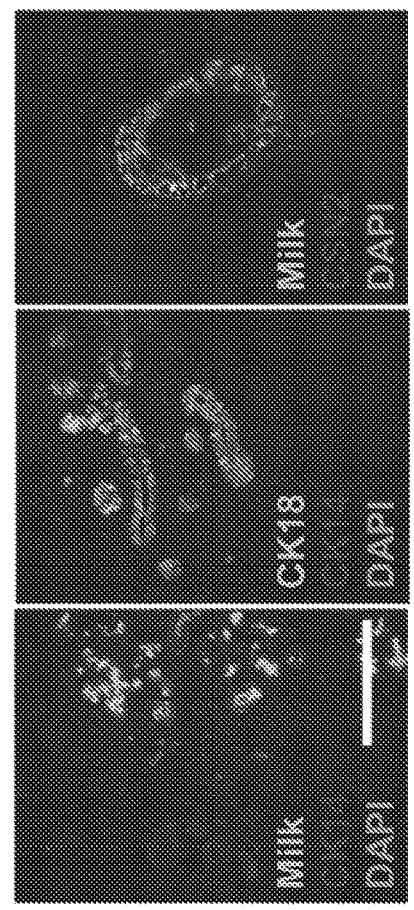
Fig. 7B
Fig. 7A

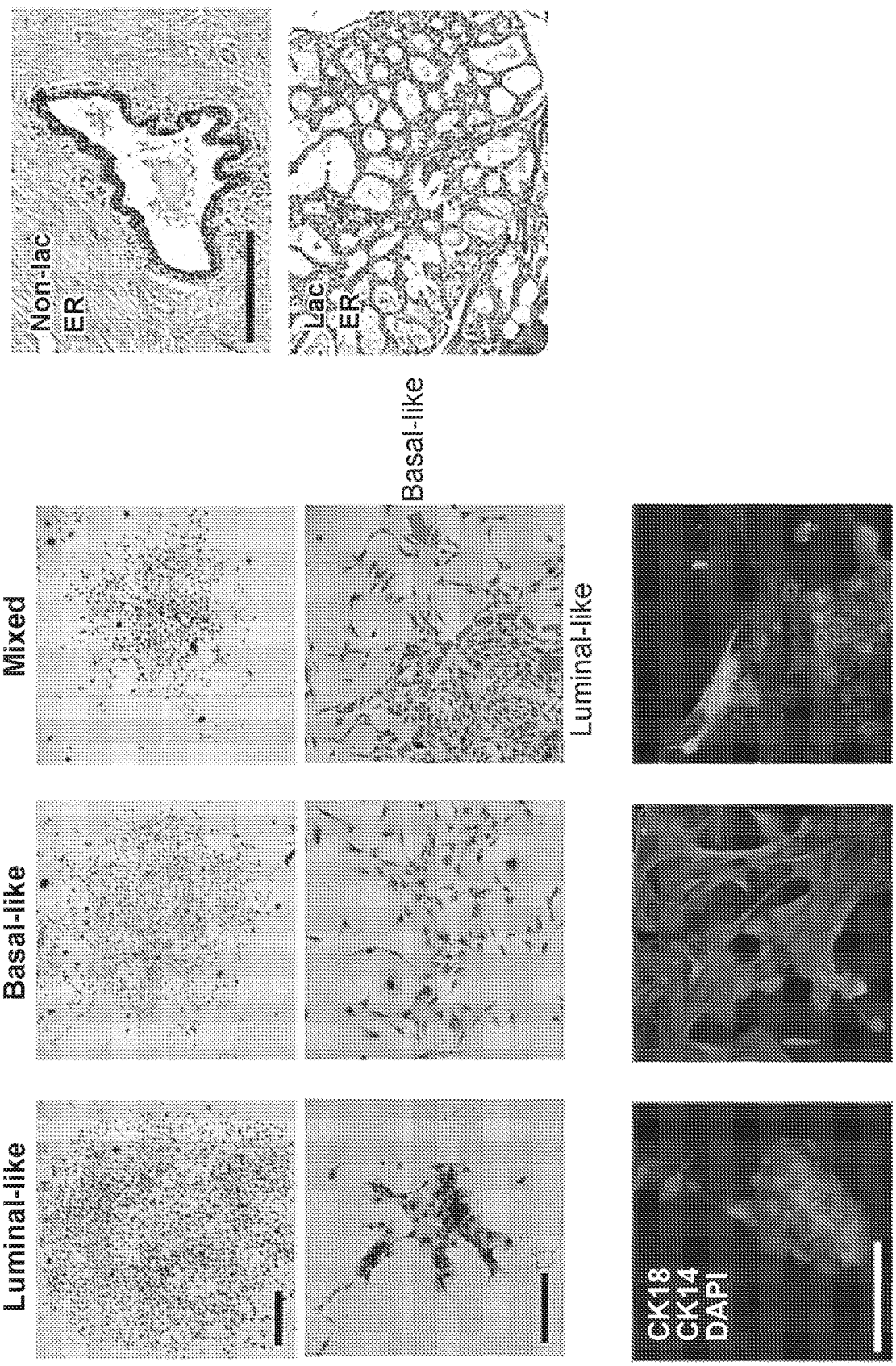

IN VITRO INDUCTION OF MAMMARY-LIKE DIFFERENTIATION FROM HUMAN PLURIPOTENT STEM CELLS

CROSS-REFERENCE TO RELATED APPLICATIONS

This application is the national phase of International Application No. PCT/US2018/015318, filed Jan. 25, 2018, which designated the U.S. and that International Application was published under PCT Article 21(2) in English. This application claims priority under 35 U.S.C. § 119(e) to U.S. Provisional Application No. 62/450,484, filed Jan. 25, 2017, the contents of which are herein incorporated by reference in their entirety.

FIELD OF THE INVENTION

Described herein are methods and compositions related to generation of mammary cells from pluripotent stem cells.

BACKGROUND

Breast cancer is the most common cancer among women in the United States. It is the second leading cause of cancer death in women, after lung cancer. About 210,000 women in the United States will be found to have breast cancer this year. About 39,840 women will die from the disease this year. Right now there are about two and a half million breast cancer survivors in the United States. Hereditary breast cancer accounts for 5-10% of total breast cancers, BRCA1 or 2 with risks up to 90% and 60%, respectively.

Understanding the pathogenesis of breast cancer would greatly improve opportunities to develop therapeutic strategies. Unfortunately, the molecular biology of early human mammary gland development is poorly understood, due in part to the lack of suitable in vitro models. Studies using mouse models have revealed that the crosstalk among certain growth factors and transcription factors as guiding specification of the mammary gland during early development. Postnatal mammary gland development is controlled by systemic and regional hormones and growth factors. Besides the aforementioned factors, extracellular matrix (ECM) also plays a key role during mammary gland development, with combinations of certain ECM proteins promoting the branching into the matrix during elongation. The observations, while informative, have largely been derived from observing primary cultures of breast cells, which are merely expanded and manipulated, but does not recapitulate the differentiation and maturation process of in vivo mammary gland formation and mammogenesis. As an alternative, induced pluripotent stem cells (iPSCs) have served as a rich source material for generating differentiated cell types and aiding understanding of developmental processes. Despite much research effort on directed differentiation of iPSCs into mammary tissue regeneration or bioengineering, no study has reported on the induction of mammary-like cells and organoids from hiPSCs.

iPSC-derived mammary-like organoids can be used to build in vitro models for pinpointing the precise effects of various factors on mammary cell transformation and breast cancer development. This would include elucidating the effect of various factors in human mammary gland and breast cancer. Thus, there is a great need in the art for techniques for producing mammary cells and tissues.

Described herein are methods and compositions for generating human mammary-like cells from iPSCs. Using a novel two-step protocol involving a suspension sphere culture system that enriches for non-neural ectoderm progenitors and a mixed gel floating 3D culture system that mimics the physical extracellular matrix (ECM) for mammary differentiation. To the Inventors' knowledge, this is the first report on derivation of mammary-like cells and organoids from hiPSCs.

SUMMARY OF THE INVENTION

Described herein is a method of generating mammary cells, including culturing induced pluripotent stem cells (iPSCs) in a culture medium for about 8-12 days to generate embryoid bodies (EBs), and differentiating the EBs into mammary cells by culturing in a differentiation medium for about 28-32 days. In other embodiments, the culture medium includes MammoCult™ medium. In other embodiments, the EBs express one or more markers selected from the group consisting of: AP-2γ, CK8 and CK18. In other embodiments, the EBs do not express one or more markers selected from the group consisting of: OTX and SOX11. In other embodiments, the EBs into mammary cells includes culturing the EBs in the presence of pTHrP, hydrocortisone, insulin, FGF10 and/or HGF. In other embodiments, the method includes culturing in the presence of pTHrP is for days 1-5, followed by culturing in the presence of hydrocortisone, insulin, FGF10 and/or HGF for days 23-27. In other embodiments, differentiating the EBs into mammary cells includes culturing in the presence of a substrate. In other embodiments, the substrate includes Collagen I and/or MATRIGEL®. In other embodiments, the differentiation medium includes EpiCult-B™ medium. In other embodiments, the mammary cells comprise breast cells, luminal cells, and basal cells. In other embodiments, the breast cells express one or more markers selected from the group consisting of: α-lactalbumin/LALBA, milk protein, and Acetyl-CoA. In other embodiments, the luminal cells express one or more markers selected from the group consisting of: EpCAM and CK18. In other embodiments, the basal cells express one or more markers selected from the group consisting of: CK14 and P63. In other embodiments, the mammary cells are lactogenic mammary cells. In other embodiments, inducing formation of lactogenic mammary cells includes culturing in the presence of insulin, prolactin and/or hydrocortisone.

Described herein is a method of generating mammary cell organoids, including culturing induced pluripotent stem cells (iPSCs) in a culture medium for about 8-12 days to generate embryoid bodies (EBs), and differentiating the EBs into mammary cell organoids by culturing in a differentiation medium including one or more substrates for about 28-32 days. In other embodiments, the culture medium includes MammoCult™ medium. In other embodiments, the EBs express one or more markers selected from the group consisting of: AP-27, CK8 and CK18 and do not express one or more markers selected from the group consisting of: OTX and SOX11. In other embodiments, differentiating the EBs into mammary cell organoids includes culturing the EBs in the presence of pTHrP for days 1-5, followed by culturing in the presence of hydrocortisone, insulin, FGF10 and/or HGF for days 23-27. In other embodiments, the one or more substrate includes Collagen I and/or MATRIGEL®. In other embodiments, the differentiation medium includes EpiCult-B™ medium. In other embodiments, the mammary cell organoids comprise breast cells that express one or more markers selected from the group consisting of: α-lactalbumin/LALBA, milk protein, and Acetyl-CoA, luminal cells that express one or more markers selected from the group consisting of: EpCAM and CK18, and basal cells that express one or more markers selected from the group consisting of: CK14 and P63. In other embodiments, the mammary cell organoids are lactogenic mammary cell organoids. In other embodiments, inducing formation of lactogenic mammary cell organoids includes culturing the mammary cell organoids in the presence of insulin, prolactin and/or hydrocortisone. In other embodiments, the mammary cells organoids comprise aveolar structures. In other embodiments, culturing iPSCs in a culture medium is for about 10 days, and differentiating the EBs in a differentiation medium is for about 30 days.

BRIEF DESCRIPTION OF FIGURES

FIG. 1. Generation of mEBs from hiPSCs. (FIG. 1A) A two-step protocol for in vitro differentiation of hiPSCs to mammary-like cells. Bars: 100 µm.

FIG. 2. IPA analysis of 5-d and 10-d mEB mRNA profiles. cDNA microarray analysis was used to profile 5-d mEBs, 10-d mEBs and control hiPSCs. Relative expression level changes were calculated comparing mEBs (5-d or 10-d) to hiPSCs. The comparison between 5-d and 10-d mEBs were based on fold changes relative to hiPSCs. (FIG. 2A) Bio function analysis using IPA shows most significant up- and down-regulated bio-functions in mEBs compared to hiPSCs. Comparison between 5-d and 10-d mEBs were performed. Activation z-score (top) and –log (P value) (bottom) are shown.

FIG. 5. related to FIG. 1: mEBs express non-neural ectoderm markers. (FIG. 5A) Cells in 10-d differentiated EBs expressed high percentage of neural marker TUJ1 but low percentage of non-neural marker CK18. 10-d EBs was attached onto MATRIGEL®-coated tissue culture plate. Phase contrast and immunofluorescence staining images are shown. (FIG. 5B) Western blot analysis of marker expression in 10-d EBs and 10-d mEBs. CK8 and CK18 are non-neural markers. SOX11 is a neural marker. GAPDH is used as loading control. (FIG. 5C) Immunofluorescence co-staining of non-neural (AP-2γ, in blue) and early neural (OTX2, in red) ectoderm markers. (FIG. 5D) mEBs formation in two other iPSC lines. Bars: 100 µm.

FIG. 6. related to FIG. 2: Functional analysis of 5-d and 10-d mEBs using IPA software.

FIG. 7. related to FIG. 3: Mammary differentiation from 10-d mEBs in 3D floating mixed gel. (FIG. 7A) Immunofluorescence co-staining of basal, luminal and breast markers in normal human breast tissues. (FIG. 7B) Immunohistochemical staining of marker expression pattern in normal human breast tissues.

FIG. 8. Related to FIG. 4: Immunohistochemical and immunofluorescence staining of markers in iPSC-derived mammary-like structures. (FIG. 8B) Representative images for luminal-like, myoepithelial-like and mixed-morphological colonies in colony formation assays. Top: images taken under 40× magnification. Middle: enlarged images taken under 100× magnification. Broken red line separate luminal-like (left) and basal-like (right) morphological cells. Bottom: representative immunofluorescent images of luminal (CK18) and basal (CK14) marker expression in the colonies. (FIG. 8C) Immunohistochemical staining of ER expression in non-lactating and lactating human breast tissues. Bars: 100 µm.

DETAILED DESCRIPTION

Figure 1B:
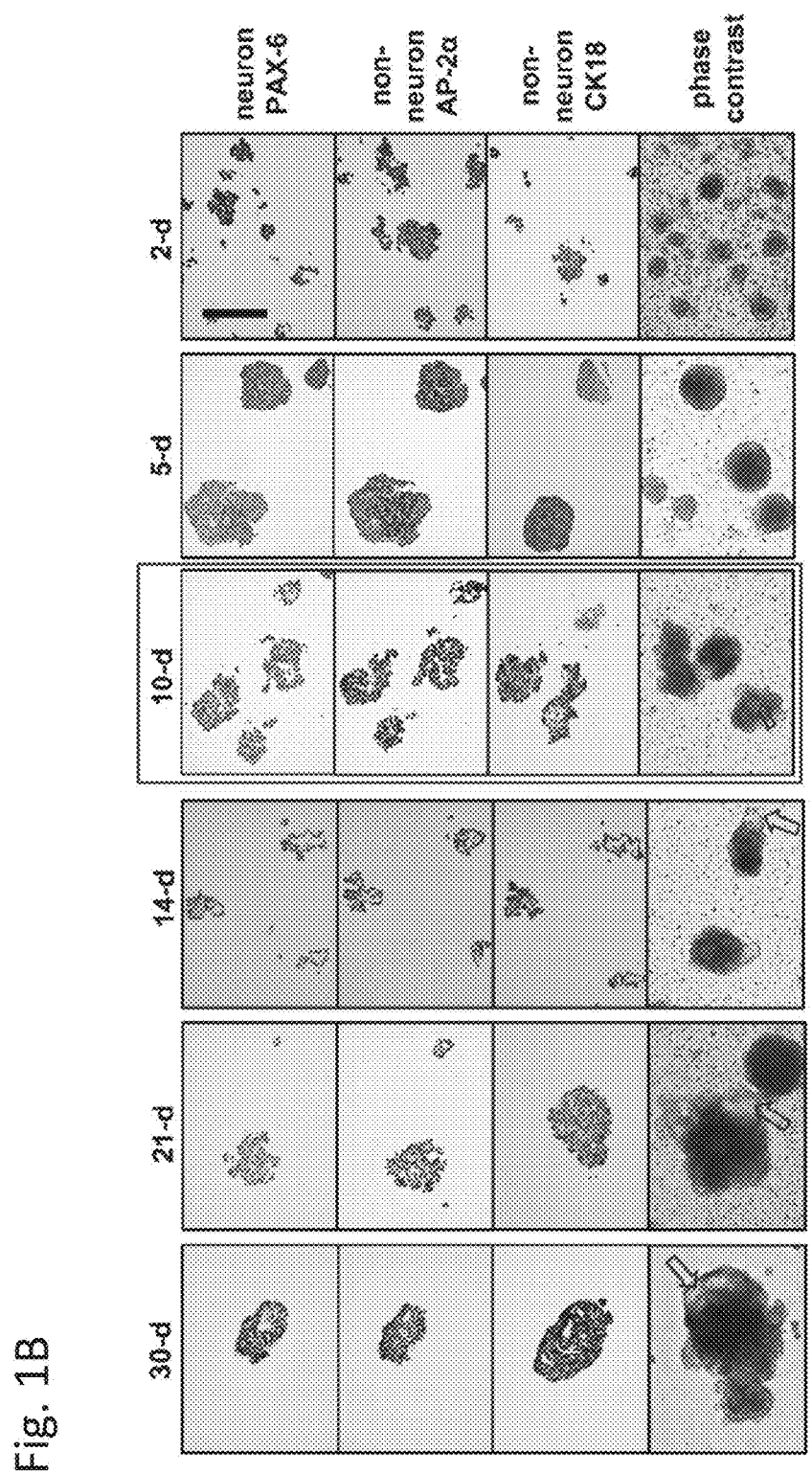
(FIG. 1B) Marker expression in differentiated mEBs at different stages. iPSCs were cultured in MammoCult medium on ultra-low attachment plates for indicated days. Spheres were collected and western blotting analysis was used to quantify marker expression. Red square: highlight of 10-d mEBs showed high non-neural ectoderm and low other lineage marker expression.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy $22^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology $3^{rd}$ ed., revised ed., J. Wiley & Sons (New York, NY 2006); Smith, March's Advanced Organic Chemistry Reactions, Mechanisms and Structure $7^{th}$ ed., J. Wiley & Sons (New York, NY 2013); Singleton, Dictionary of DNA and Genome Technology $3^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application. For references on how to prepare antibodies, see Greenfield, Antibodies A Laboratory Manual $2^{nd}$ ed., Cold Spring Harbor Press (Cold Spring Harbor NY, 2013); Köhler and Milstein, Derivation of specific antibody-producing tissue culture and tumor lines by cell fusion, Eur. J. Immunol. 1976 Jul., 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As described, hereditary breast cancer includes mutations in BRCA1 and 2. The BRCA1 phenotype present early, characteristic loss of TP53, PTEN in 60-90% of tumors preceding loss of heterozygosity, extreme genomic instability, and sensitivity to DNA cross-linking agents. Interestingly, BRCA1 mutations appear to possess basal-like subtype properties, whereas BRCA2 mutation present luminal subtype properties. Whereas basal-like BRCA1 mutations (e.g., triple negative ER-/PR-/Her2-) are aggressive with high growth rate, mesenchymal properties, brain metastasis and lymphatic spread, BRCA2 mutations are indolent and responsive to treatment. Deciphering the impact of tissue tropism on these different cancer subtypes would greatly aid identification of points of control for therapeutic intervention. In this context, an understanding of the underlying cellular developmental context is greatly needed.

Induced pluripotent stem cells (iPSCs) can be generated directly from terminally differentiated cells. Not only can they bypass the need for embryos, but they also enable patient-specific or personalized disease modeling using iPSCs from each individual. Human iPSCs (hiPSCs) can give rise to multiple cell types such as neurons, cardiomyocytes, and hepatocytes. Despite much research effort on directed differentiation of iPSCs in vitro and tremendous interest in mammary tissue regeneration or bioengineering, no study has reported on the induction of mammary-like cells and organoids from hiPSCs using in vitro systems.

Taking a cue from the Inventors' understanding of human embryonic mammary gland development, the Inventors conceptualized that the first step for in vitro induction of mammary differentiation from hiPSCs was to pattern iPSCs to non-neural ectoderm, thus enriching mammary progenitors. Formation of embryoid bodies (EBs) from iPSCs is a well-known and broadly used method for three-germ layer differentiation, mimicking in vivo embryo development. However, this method preferentially induces neural ectoderm from iPSCs and embryonic stem cells. Although neural and non-neural ectoderm cells co-exist at the same embryonic stage, in vitro studies have shown that the "default" differentiation for iPSCs is the neural lineage. To convert iPSCs to cells and organoids specific to tissues originating from non-neural ectoderm, a protocol that first enriches non-neural ectoderm cells is an important step.

Although the molecular biology of early human mammary gland development is poorly understood, studies using mouse models have revealed that the crosstalk among FGF/FGFR, TBX3, NRG3/ERBB4, and Wnt/LEF1 signaling is critical for the specification of the mammary gland during early development. In addition, BMP4 may interact with pTHrP signaling and play an essential role in early embryonic mammary gland commitment and subsequent development while inhibiting hair follicle development. Postnatal mammary gland development is controlled by systemic and regional hormones and growth factors. In vitro studies have revealed that growth factors such as insulin-like growth factor 1 (IGF-1), epidermal growth factor (EGF), fibroblast growth factor (FGF) and hepatocyte growth factor (HGF) are critical in the growth, differentiation and maturation of mammary epithelial cells. Additionally, ectodysplasin/NF-κB signaling is fundamental for embryonic hormone-independent mammary ductal growth by inducing pTHrP, Wnt, and EGF signals. Besides the aforementioned factors, extracellular matrix also plays a key role during mammary gland development. Previous studies showed that the combination of MATRIGEL® and Collagen I promotes the branching but no protrusions into the matrix during elongation.

While informative, the above report observations have largely been obtained using primary breast cells obtained from biopsy samples. A key limitation of this in vitro platform is that primary cells in culture merely represent expansion and manipulation of the original isolated cells. This does not allow for the multiplicity of features that occur during in vivo developmental and maturation stages. This includes the participation of multiple cell populations, formation of relevant structures, and proper functional acquisition. In this aspect, the Inventors believe iPSCs will provide a superior platform to study mammary development and maturation by essentially recapitulating a multiplicity of features that occur during in vivo developmental and maturation stages. iPSC-derived mammary cells and mammary cell organoids can present a great deal more complexity with higher relevancy for modeling in a way that primary breast cells cannot.

Herein, the Inventors attempted to exploit the Inventors' current knowledge on mammary gland development to develop a reliable method for generating human mammary-like cells from iPSCs. The Inventors introduced a novel two-step protocol involving a suspension sphere culture system that enriches for non-neural ectoderm progenitors and a mixed gel floating 3D culture system that mimics the physical extracellular matrix (ECM) for mammary differentiation. To the Inventors' knowledge, this is the first report on derivation of mammary-like cells and organoids from hiPSCs.

Described herein is a method of generating mammary cells, including culturing pluripotent stem cells (PSCs) in a culture medium for about 8-12 days to generate embryoid bodies (EBs) and differentiating the EBs into mammary cells by culturing in a differentiation medium for about 23-32 days. In various embodiments, the pluripotent stem cells are embryonic stem cells (ESCs). In various embodiments, the pluripotent stem cells are induced pluripotent stem cells (iPSCs). In other embodiments, culturing induced pluripotent stem cells (iPSCs) in a culture medium is for about 8, 9, 10, 11, or 12 days to generate embryoid bodies (EBs). In other embodiments, culturing induced pluripotent stem cells (iPSCs) in a culture medium is for about 10 days to generate embryoid bodies (EBs). In other embodiments, differentiating the EBs into mammary cells by culturing in a differentiation medium is for about 30 days. In other embodiments, differentiating the EBs into mammary cells by culturing in a differentiation medium is for about 23, 24, 25, 26, 27, 28, 29, 30, 31, or 32 days. In other embodiments, the culture medium enriches for non-neural ectoderm cells. In other embodiments, the culture medium includes MammoCult™ medium, a defined, serum-free culture medium. In other embodiments, the EBs express one or more markers selected from the group consisting of: AP-2γ, CK8 and CK18. In other embodiments, the EBs express one or more markers selected from the group consisting of: AP-2a, AP-2γ, P63, CK8, and CK18. In other embodiments, the EBs express high levels of non-phospho (Ser33/37/Thr41) β-Catenin (Active) and p-p 65 (Ser536). In other embodiments, the EBs do not express one or more markers selected from the group consisting of: OTX and SOX11. In other embodiments, the EBs do not express one or more markers selected from the group consisting of: FOXG1, TUJ1, OTX2, SOX11, and PAX6. In other embodiments, differentiating the EBs into mammary cells includes culturing the EBs in the presence of parathyroid hormone (pTHrP), hydrocortisone, insulin, FGF10 and/or HGF. In other embodiments, culturing in the presence of pTHrP is for days 1-5, followed by culturing in the presence of hydrocortisone, insulin, FGF10 and/or HGF for days 23-27. In various embodiments, pTHrP is at a concentration of about 50-150 ng/ml. In various embodiments, pTHrP is at a concentration of about 100 ng/ml. In various embodiments, hydrocortisone is at a concentration of about 0.5-1.5 µg/ml, insulin is at a concentration of about 5-15 µg/ml, FGF10 is at a concentration of about 25-75 ng/ml, and HGF is at a concentration of about 25-75 ng/ml. In various embodiments, hydrocortisone is at a concentration of about 1 µg/ml, insulin is at a concentration of about 10 µg/ml, FGF10 is at a concentration of about 50 ng/ml, and HGF is at a concentration of about 50 ng/ml. In other embodiments, differentiating the EBs into mammary cells includes culturing in the presence of a substrate. In other embodiments, the substrate includes extracellular matrix (ECM) proteins. In other embodiments, the substrate includes Collagen I and/or MATRIGEL®. In various embodiments, MATRIGEL® is at a concentration of about 1.5-3.5 mg/mL. In various embodiments, Collagen I is at a concentration of about 0.5-1.5 mg/mL. In various embodiments, MATRIGEL® is at a concentration of about 2.5 mg/mL. In various embodiments, Collagen I is at a concentration of about 1 mg/mL. In other embodiments, the differentiation medium includes EpiCult-B™ medium, a defined serum-free culture medium. In other embodiments, the mammary cells include breast cells, luminal cells, and basal cells. In other embodiments, breast cells express one or more markers selected from the group consisting of: α-lactalbumin/LALBA, milk protein, and Acetyl-CoA. In other embodiments, luminal cells express one or more markers selected from the group consisting of: EpCAM and CK18. In other embodiments, basal cells express one or more markers selected from the group consisting of: CK14 and P63. In other embodiments, the mammary cells are lactogenic mammary cells. In other embodiments, inducing formation of lactogenic mammary cells includes culturing in the presence of insulin, prolactin and/or hydrocortisone. In various embodiments, the cells are organized as an organoid including aveolar and acinar structures. In various embodiments, mammary cells made by the described method are transplanted into a subject. In various embodiments, the mammary cells are autologous. In various embodiments, the mammary cells are allogenic.

For example, iPSCs are induced to form EBs by suspension culturing in a culture medium such as complete Mammocult™ medium. After iPSCs are cultured in Mammocult™ medium for 10 days, the 10-day old EBs are mixed with MATRIGEL® (2.5 mg/mL)/Collagen I (1 mg/mL) gel on the Nunclon delta surface culture plate (Sigma). Mixed gel can be made by mixing 3 portions of 10.1 mg/ml MATRIGEL® with 1 portion of 4 mg/ml Collagen I. After being solidified, the mixed gel is detached and additional culture medium is added to floating cells in culture. The culture medium can be changed every 3 days. To induce differentiation of the EBs into mammary cells, floating gels are cultured in complete Epicult-B™ medium supplemented with parathyroid hormone (pTHrP, 100 ng/ml) for 5 days. To induce mammary-like ductal branches and alveolar differentiation, the gels are then cultured in complete Epicult-B™ medium supplemented with hydrocortisone (1 µg/ml), insulin (10 µg/ml), FGF10 (50 ng/ml), and HGF (50 ng/ml) for 20 days. To induce milk protein expression in lactogenic medium, prolactin (10 µg/ml), hydrocortisone (1 µg/ml), and insulin (10 µg/ml) are added to complete Epicult-B™ medium supplemented with 10% Fetal Bovine Serum (FBS) for 5 days.

Described herein is a method of generating mammary cell organoids, including culturing pluripotent stem cells (PSCs) in a culture medium for about 8-12 days to generate embryoid bodies (EBs), and differentiating the EBs into mammary cell organoids by culturing in a differentiation medium including one or more substrates for about 23-32 days. In various embodiments, the pluripotent stem cells are embryonic stem cells (ESCs). In various embodiments, the pluripotent stem cells are induced pluripotent stem cells (iPSCs). In other embodiments, differentiating the EBs into mammary cells by culturing in a differentiation medium is for about 23, 24, 25, 26, 27, 28, 29, 30, 31, or 32 days. In other embodiments, culturing induced pluripotent stem cells (iPSCs) in a culture medium is for about 8, 9, 10, 11, or 12 days to generate embryoid bodies (EBs). In other embodiments, culturing induced pluripotent stem cells (iPSCs) in a culture medium is for about 10 days to generate embryoid bodies (EBs). In other embodiments, differentiating the EBs into mammary cells by culturing in a differentiation medium is for about 30 days. In other embodiments, the culture medium enriches for non-neural ectoderm cells. In other embodiments, the culture medium includes MammoCult™ medium, a defined, serum-free culture medium. In other embodiments, the EBs express one or more markers selected from the group consisting of: AP-2a, AP-2γ, P63, CK8, and CK18. In other embodiments, the EBs express high levels of non-phospho (Ser33/37/Thr41) β-Catenin (Active) and p-p 65 (Ser536). In other embodiments, the EBs do not express one or more markers selected from the group consisting of: OTX and SOX11. In other embodiments, the EBs do not express one or more markers selected from the group consisting of: FOXG1, TUJ1, OTX2, SOX11, and PAX6. In other embodiments, the EBs express one or more markers selected from the group consisting of: AP-2γ, CK8 and CK18 and do not express one or more markers selected from the group consisting of: OTX and SOX11. In other embodiments, differentiating the EBs into mammary cell organoids includes culturing the EBs in the presence of pTHrP for days 1-5, followed by culturing in the presence of hydrocortisone, insulin, FGF10 and/or HGF for days 23-27. In various embodiments, pTHrP is at a concentration of about 50-150 ng/ml. In various embodiments, pTHrP is at a concentration of about 100 ng/ml. In various embodiments, hydrocortisone is at a concentration of about 0.5-1.5 µg/ml, insulin is at a concentration of about 5-15 µg/ml, FGF10 is at a concentration of about 25-75 ng/ml, and HGF is at a concentration of about 25-75 ng/ml. In various embodiments, hydrocortisone is at a concentration of about 1 µg/ml, insulin is at a concentration of about 10 µg/ml, FGF10 is at a concentration of about 50 ng/ml, and HGF is at a concentration of about 50 ng/ml. In other embodiments, the one or more substrates include extracellular matrix (ECM) proteins. In other embodiments, the one or more substrates include Collagen I and/or MATRIGEL®. In other embodiments, the substrate includes Collagen I and/or MATRIGEL®. In various embodiments, MATRIGEL® is at a concentration of about 1.5-3.5 mg/mL. In various embodiments, Collagen I is at a concentration of about 0.5-1.5 mg/mL. In various embodiments, MATRIGEL® is at a concentration of about 2.5 mg/mL. In various embodiments, Collagen I is at a concentration of about 1 mg/mL. In other embodiments, the differentiation medium includes EpiCult-B™ medium, a defined serum-free culture medium. In other embodiments, the mammary cell organoids include breast cells that express one or more markers selected from the group consisting of: α-lactalbumin/LALBA, milk protein, and Acetyl-CoA, luminal cells that express one or more markers selected from the group consisting of: EpCAM and CK18, and basal cells that express one or more markers selected from the group consisting of: CK14 and P63. In other embodiments, the mammary cell organoids are lactogenic mammary cell organoids. In other embodiments, the organoids include one or more cells expressing EpCAM/CD49f$^+$, EpCAM$^+$/CD49f$^-$, EpCAM$^-$/CD49f$^+$, and EpCAM$^-$/CD49f$^-$. In other embodiments, inducing formation of lactogenic mammary cell organoids includes culturing the mammary cell organoids in the presence of insulin, prolactin and/or hydrocortisone. In other embodiments, the mammary cells organoids include aveolar structures. In other embodiments, the mammary cells organoids include acinar structures.

For example, iPSCs are induced to form EBs by suspension culturing in a culture medium such as complete Mammocult™ medium. After iPSCs are cultured in Mammocult™ medium for 10 days, the 10-day old EBs are mixed with MATRIGEL® (2.5 mg/mL)/Collagen I (1 mg/mL) gel. Solidified mixed gel is detached and additional culture medium is added to floating cells in culture and culture medium can be changed every 3 days. Differentiation of the EBs into mammary cells, include culture of floating gels in complete Epicult-B™ medium supplemented with parathyroid hormone (pTHrP, 100 ng/ml) for 5 days. To induce mammary-like ductal branches and alveolar differentiation, the gels are then cultured in complete Epicult-B™ medium supplemented with hydrocortisone (1 µg/ml), insulin (10 µg/ml), FGF10 (50 ng/ml), and HGF (50 ng/ml) for 20 days. To induce milk protein expression in lactogenic medium, prolactin (10 µg/ml), hydrocortisone (1 µg/ml), and insulin (10 µg/ml) are added to complete Epicult-B™ medium supplemented with 10% Fetal Bovine Serum (FBS) for 5 days.

Described herein is a method of reconstructing a mammary gland in a subject including, generating an induced pluripotent stem cell line (iPSC) from a subject, differentiating iPSCs to mammary cells, transplanting the mammary cells into the subject. In various embodiments, differentiating iPSCs to mammary cells includes culturing the iPSCs in a culture medium for about 8-12 days to generate embryoid bodies (EBs) and differentiating the EBs into mammary cells by culturing in a differentiation medium for about 23-32 days.

Example 1

Human Tissues

This study was approved by the Institutional Review Board (IRB) at Cedars-Sinai Medical Center. Normal human breast tissues were obtained from prophylactic surgeries with written informed consent.

Example 2

Culture of MammoCult-Derived Embryoid Bodies (mEBs)

To generate mEBs, iPSCs were lifted using Accutase (Innovative Cell Technologies, Inc., San Diego, CA) and suspended in the complete MammoCult™ medium (StemCell Technologies), which was composed of the basal medium, proliferation supplements, heparin (4 µg/mL), and hydrocortisone (0.48 µg/mL).

Example 3

Mammary-Like Organoid Differentiation 3D culture was performed by embedding 10-d mEBs in mixed MATRIGEL® (2.5 mg/mL)/Collagen I (1 mg/mL) gel on the Nunclon delta surface culture plate (Sigma). The mammary differentiation was divided into three stages using complete EpiCult B™ medium supplemented with different hormone and growth factors. All 3 iPSC lines formed mammary organoids with similar efficiency with the described protocol. Detailed information is provided in supplemental information.

Example 4

Statistical Analysis

Values represent mean±standard deviation (SD) of samples measured by three independent experiments. Quantitative data were analyzed using the Student's t test and two-tailed distribution. Correlations between groups were analyzed by calculating the Pearson's correlation coefficient (r) using the IBM SPSS statistics 20.0 program. Log-rank tests were performed to determine statistical significance. A P-value <0.05 was considered significant.

Example 5 mEB Culture Enriching Non-Neural Ectoderm Cells

To direct human mammary lineage differentiation from iPSCs, the Inventors developed a two-step procedure which consisted of mEB culture (step 1) and 3D mixed floating gel culture (step 2) (FIG. 1A). The Inventors intended to first enrich non-neural ectoderm cells, the origin of mammary stem cells. Embryoid bodies (EBs) at day 5-10 post-iPSC differentiation are known to highly enrich for neural ectoderm stem cells. Considering that non-neural ectoderm cells co-exist with neural ectoderm stem cells at similar embryonic stages, the Inventors examined TUJ1 and CK18 expression as neural and non-neural ectoderm stem cell markers, respectively, in EBs at day 10. When those EBs were attached onto MATRIGEL®-coated plates, the majority of the cells expressed TUJ1 as opposed to a few cells expressing CK18 (FIG. 5A). The Inventors then tested another suspension culture method for EBs using the complete MammoCult™ medium, which was reported to enrich normal mammary stem cells and breast cancer stem cells. The Inventors postulated that this might specifically enrich for stem cells that can further differentiate to cells of the mammary lineage. To this end, EBs and mEBs at day 10 were collected. Western blotting showed that mEBs expressed CK8 and CK18 but not SOX11, a neuron progenitor marker (FIG. 5B). In contrast, EBs expressed high levels of SOX11, but lacked CK8 and CK18 expression. Likewise, immunofluorescence staining demonstrated that EBs contained a large percentage of cells expressing the neural ectoderm marker OTX2, while mEBs exhibited the non-neural ectoderm marker AP-2γ (FIG. 5C).

Figure 1C:
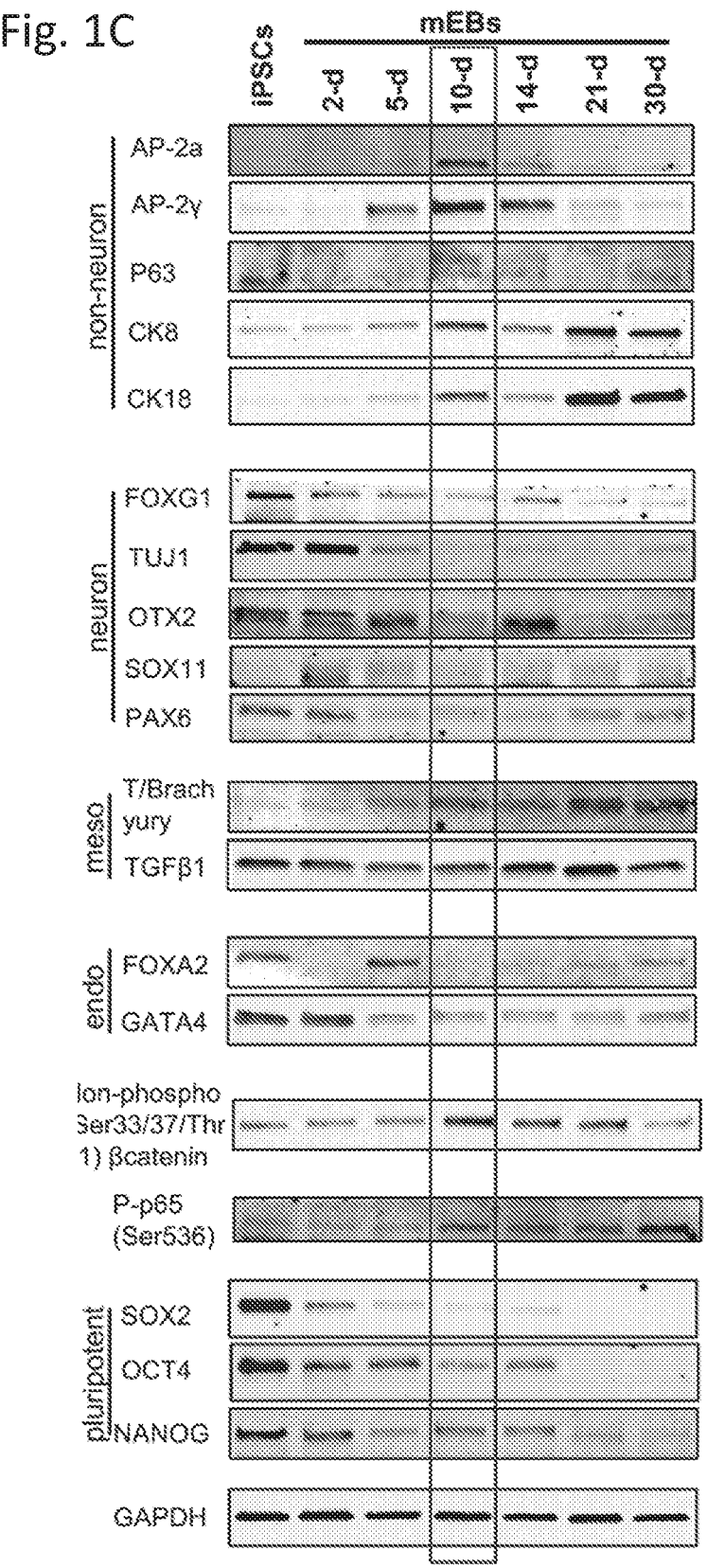
(FIG. 1C) Immunohistochemical staining of neural and non-neural marker expression in mEBs collected at indicated days. Morphologies are shown in phase contrast images. Red arrows: cavity in mEBs. Bar: 100 µm.

To determine the optimal time points of mEB culture that harbors the maximum percentage of non-neural ectoderm stem cells, iPSCs were cultured in suspension with MammoCult™ medium for 30 days and mEBs were collected at different days to evaluate their differentiation state. The Inventors performed immunohistochemical (IHC) staining to examine the differential expression of non-neural (AP-2α and CK18) and neural ectoderm (PAX6) markers in mEBs of different days (FIG. 1). Of note, iPSCs aggregated and formed solid spheres from day 2, and cavities started to appear from day 10 (FIG. 1B, right panel, red arrows). This phenotype was observed in different donor-derived iPSC lines (FIG. 5D). To better assess the quantitative changes of embryonic development markers in the 30-d mEB culture period, the Inventors also performed western blotting. As shown in FIG. 1C, markers for non-neural ectoderm differentiation, such as AP-2a, AP-2γ, P63, CK8, and CK18, were highly induced in 10-d mEBs. In contrast, neural (FOXG1, TUJ1, OTX2, SOX11, and PAX6), early mesoderm (T/Brachyury, TGFβ1), and endoderm (FOXA2, GATA4) markers were decreased, unchanged, or mildly increased. Activation of canonical Wnt (Hens and Wysolmerski, 2005) and NF-κB have been associated with mammary lineage differentiation. In line with these previous findings, high levels of non-phospho (Ser33/37/Thr41) β-Catenin (Active) and p-p 65 (Ser536), indicative of Wnt and NF-κB activation, were also detected in 10-d mEBs (FIG. 1C). As expected, expression of pluripotent markers (NANOG, OCT4, SOX2) were dramatically reduced at the same time point (FIG. 1C). Taken together, the Inventors' data suggest that mEB culture, contrary to regular EB culture, enriches for non-neural ectoderm cells.

Example 6

Ingenuity Pathway Analysis (IPA) of the mRNA Profiles of mEB mRNA Profiles

The Inventors then performed cDNA microarray analysis to examine transcriptomic profiles of 5-d and 10-d mEBs and to determine whether the Inventors could predict the forthcoming differentiation potential relative to iPSCs. The differentially expressed genes were subjected to IPA analysis for exploring the molecular basis of mEB differentiation. Three analyses including bio functions (to compare activation or inhibition of critical biological processes or functions), upstream regulators (to compare predicted molecules or signals upstream of the observed gene expression changes), and regulatory network construction based on the above analysis were performed (see the Supplemental Methods section for detailed description). Activation z score calculated by IPA was herein employed to quantitatively evaluate the activation (positive numbers shown in red) and inhibition (negative numbers shown in blue).

Figure 2B:
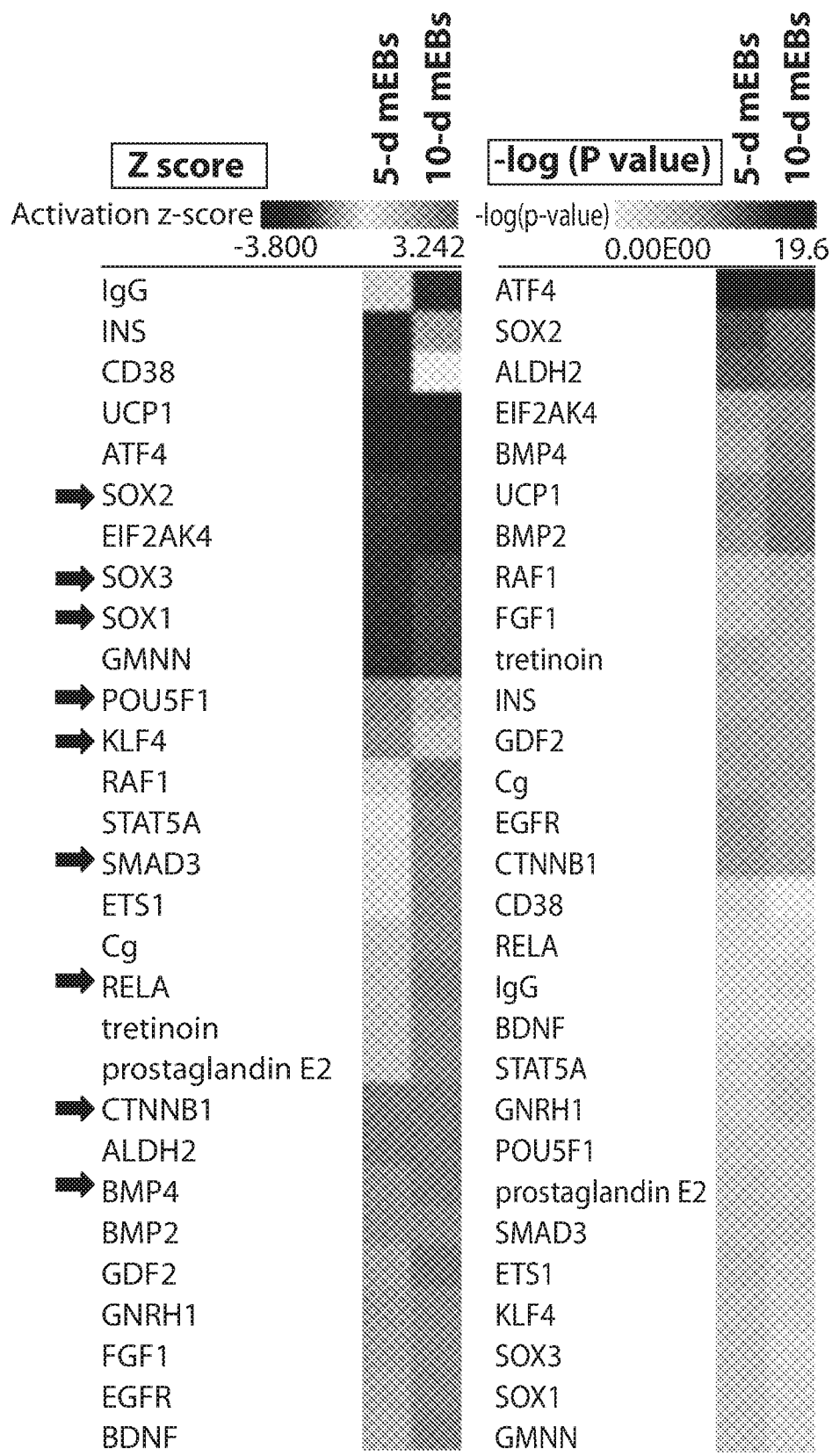
(FIG. 2B) Upstream Regulator Analysis was performed to compare 5-d and 10-d mEBs. Activation z-score (left) and –log (P value) (right) are shown.

First, bio function analysis showed that both 5-d and 10-d mEBs possessed activated bio functions including development of epithelial tissue, formation of gland, and growth of mammary gland (FIG. 2A). Compared to 5-d mEBs, 10-d mEBs showed higher activation z-scores, suggesting 10-d mEBs harbored a greater effect on the aforementioned bio functions. Next, the Inventors analyzed the upstream regulators to examine whether known developmental regulators in mammary differentiation were activated in mEBs. SOX1, 2, 3 transcriptional factors were inhibited in 5-d and 10-d mEBs, suggesting that the early commitment of neural differentiation was inhibited (FIG. 2B, blue arrows). Molecules involved in BMP, Wnt/β-catenin and NF-κB activation, such as BMP4, RELA, CTNNB1 and SMAD3, were more activated in 10-d relative to 5-d mEBs (FIG. 2B, red arrows). Pluripotency markers, POU5F1/OCT4 and KLF4, were less activated in 10-d relative to 5-d mEBs (FIG. 2B, orange arrows). Interestingly, the absolute "z score" for most of the upstream regulators were higher in 10-d mEBs compared to 5-d mEBs, indicating greater inhibitive or activating effects of these regulators in 10-d mEBs.

Figure 2C:
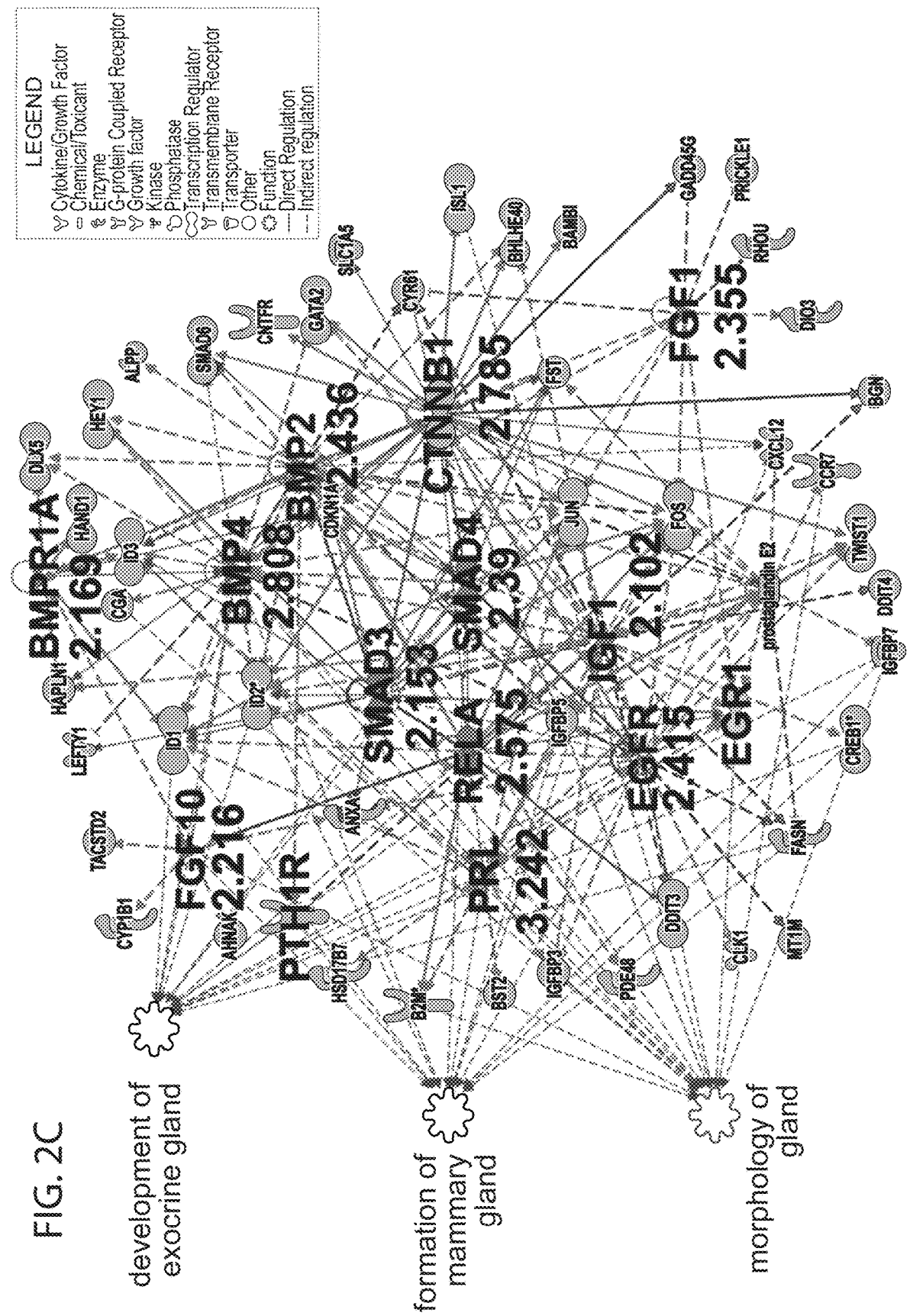
(FIG. 2C) Regulatory network constructed by selected activated upstream regulators and their associated downstream differentially-expressed genes in 10-d mEBs predicts biological functions such as mammary gland formation, morphology of gland, and development of exocrine gland. Red numbers: the activation Z score for each upstream regulator. Genes in purple color are known factors in mammary lineage commitment.
Figure 6A:
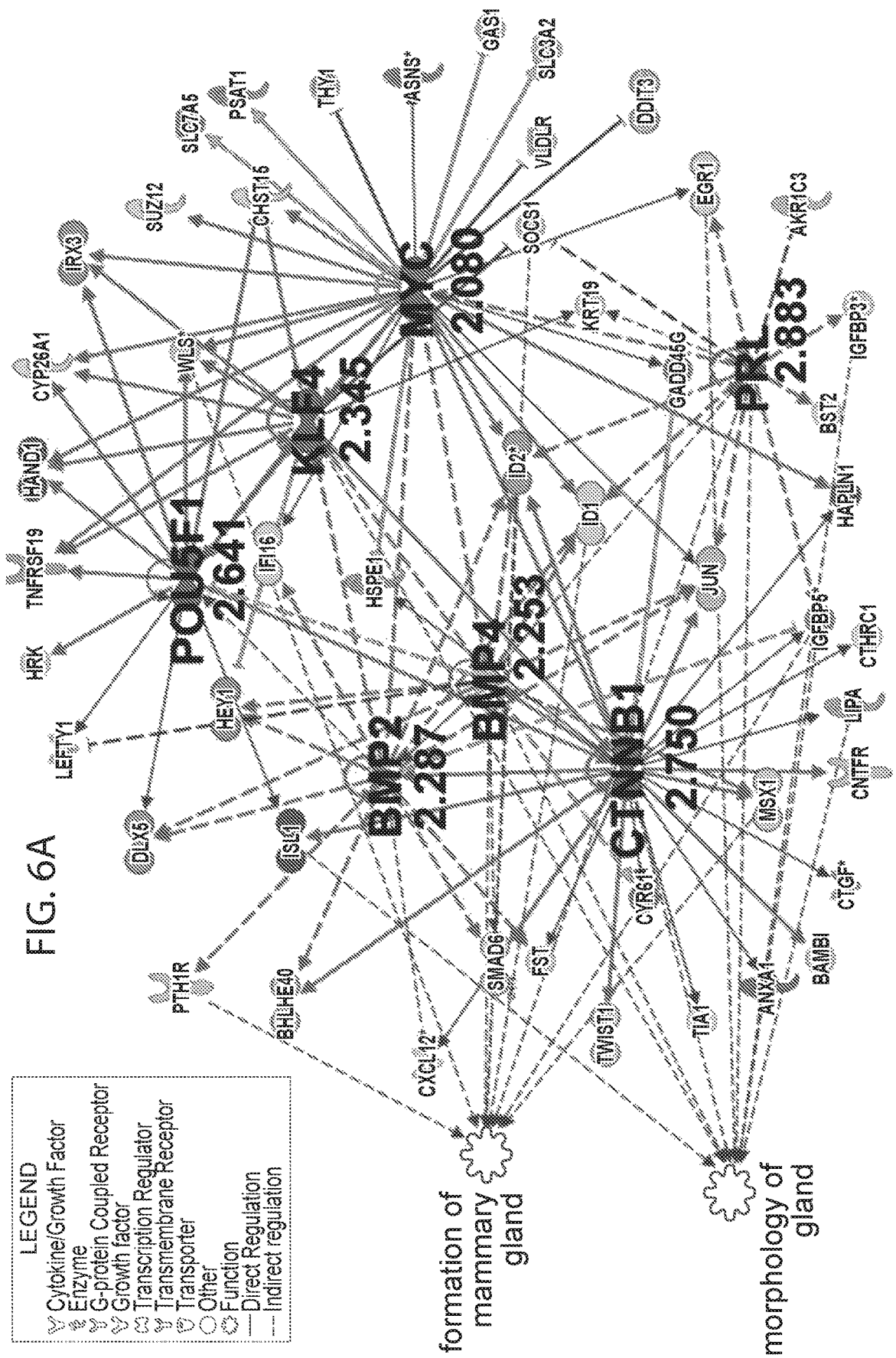
(FIG. 6A) Mechanistic networks showed the activation of signaling pathways that predicted mammary gland formation in 5-d mEBs. Blue under lines: up-regulators predicted by IPA based on known knowledge and input 10-d mEBs cDNA microarray dataset. Red numbers: the activation z score for each regulator. Genes in red color are known factors in mammary lineage commitment.
Figure 6B:
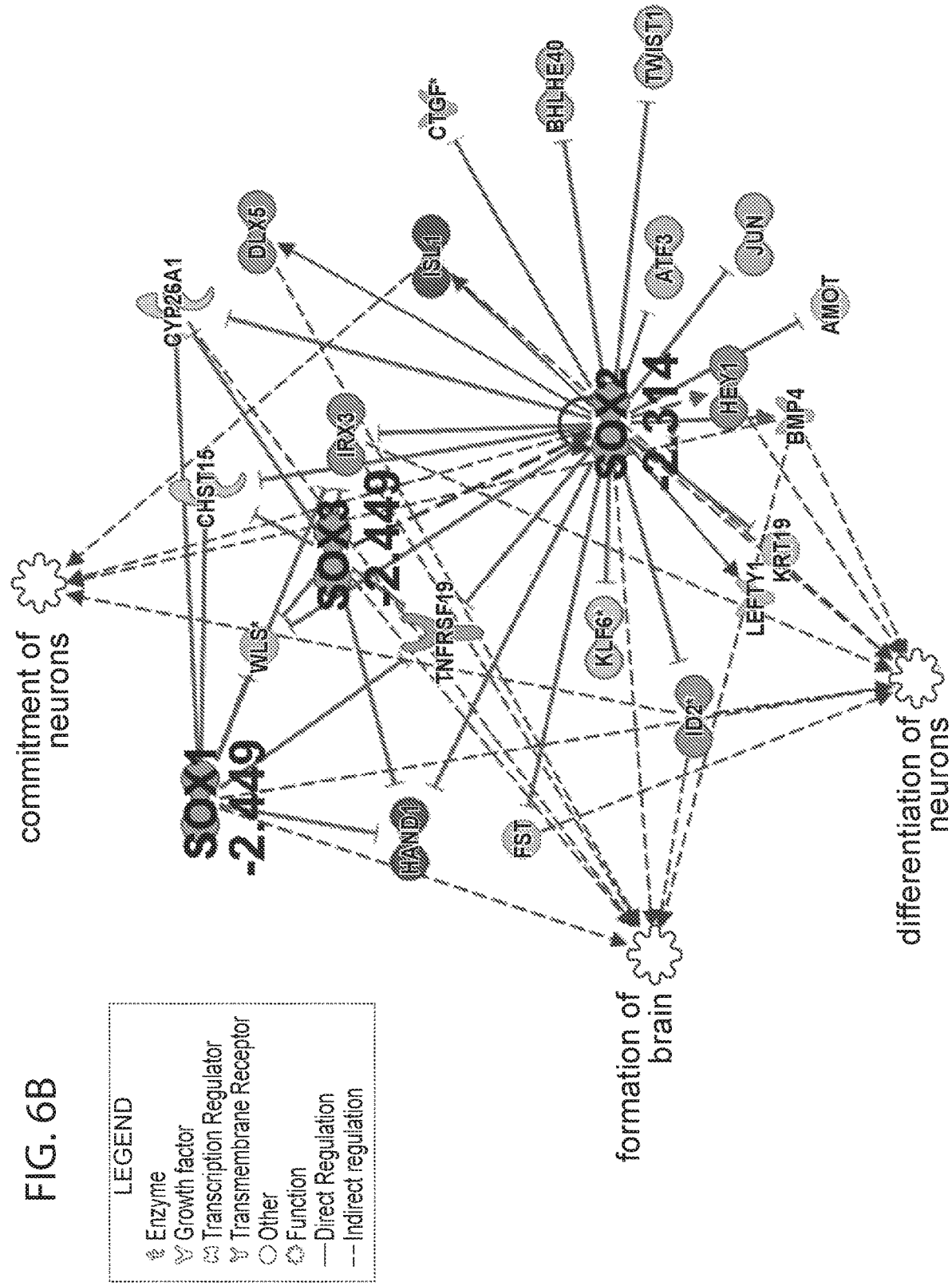
(FIG. 6B) Mechanistic networks showed the inhibition of signaling pathways that predicted neural differentiation in 5-d mEBs.
Figure 6C:
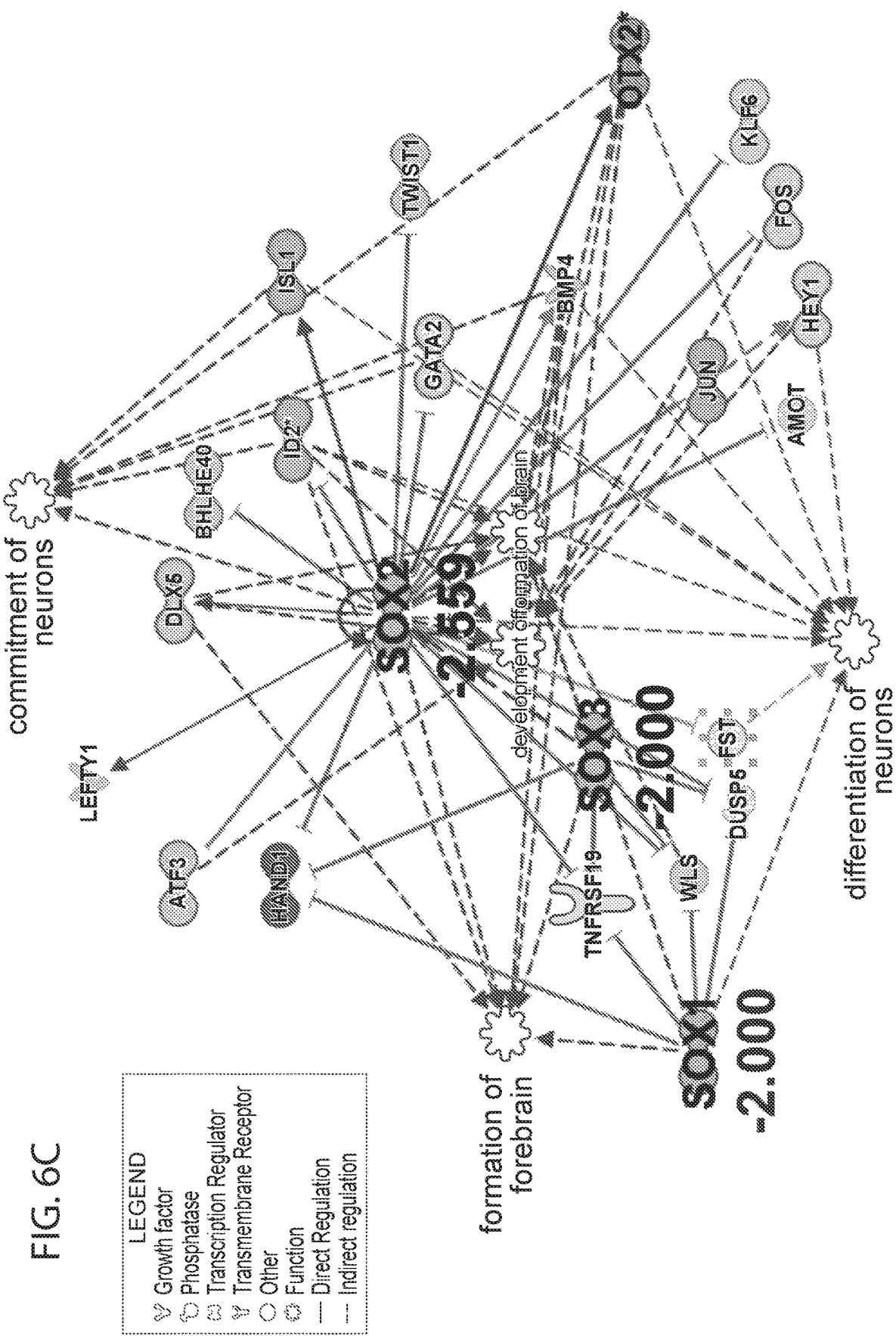
(FIG. 6C) Mechanistic networks showed the inhibition of signaling pathways that predict neural differentiation in 10-d mEBs.

The Inventors further performed regulatory network construction to uncover the intrinsic links within gene expression profiles, bio functions, and upstream regulators. Combining the prediction from analysis of upstream regulators (predicted based on the known knowledge from IPA) and differential gene expression levels (cDNA microarray analysis of mEBs), the Inventors showed that 5-d mEBs predicted formation of mammary gland (FIG. 6A). However, 10-d mEBs had greater potential predicting mammary gland formation, suggested by more involved upstream regulators and more complicated network (FIG. 2C). As expected, both 5-d (FIG. 6B) and 10-d (FIG. 6C) mEBs showed inhibition of neural lineage commitment. Collectively, the Inventors' findings suggest that 10-d mEBs had a greater differentiation potential for further mammary gland lineage commitment.

Example 7

Generation of Mammary-Like Organoids in 3D Culture

Figure 3A:
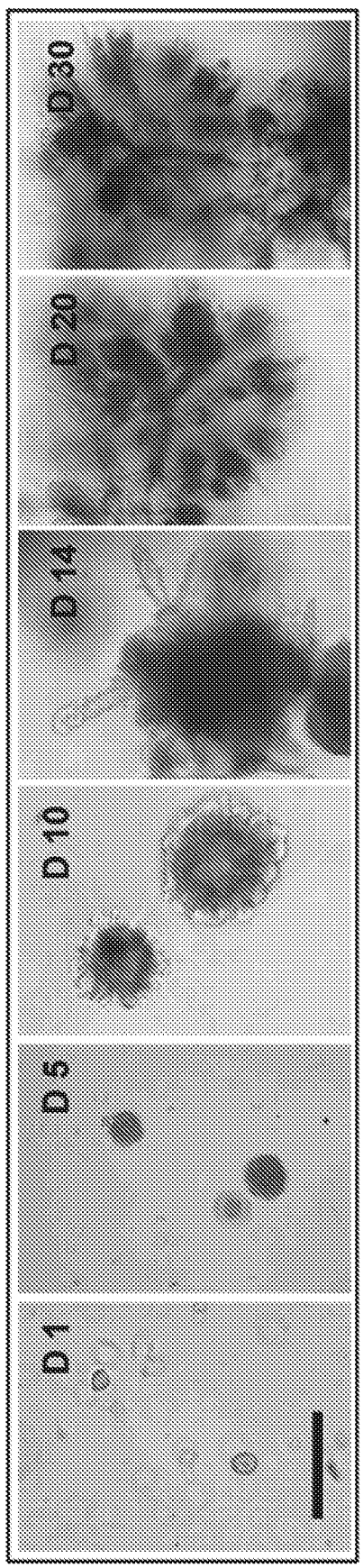
FIG. 3. Mammary differentiation from 10-d mEBs in 3D floating mixed gel. 3D structures formed by primary mouse mammary organoids (FIG. 3A) and primary human mammary organoids (FIG. 3B) cultured in 3D floating mixed gel.
(FIG. 3C) Culture of 10-d mEBs in 3D floating mixed gel.
(FIG. 3D) Immunohistochemical staining of breast, basal and luminal marker expression in differentiated mammary-like structures (from 83iCTR-n1 hiPSC line). Red circles: mammary-like structures. Yellow circles: keratinocyte-like cells. Whole mount staining was performed using DAPI to show nuclei and F-actin-AF555 to show actin structure. Images were taken using con-focal microscopy followed by the Z-stack process. Bars: 100 µm.
Figure 3B:
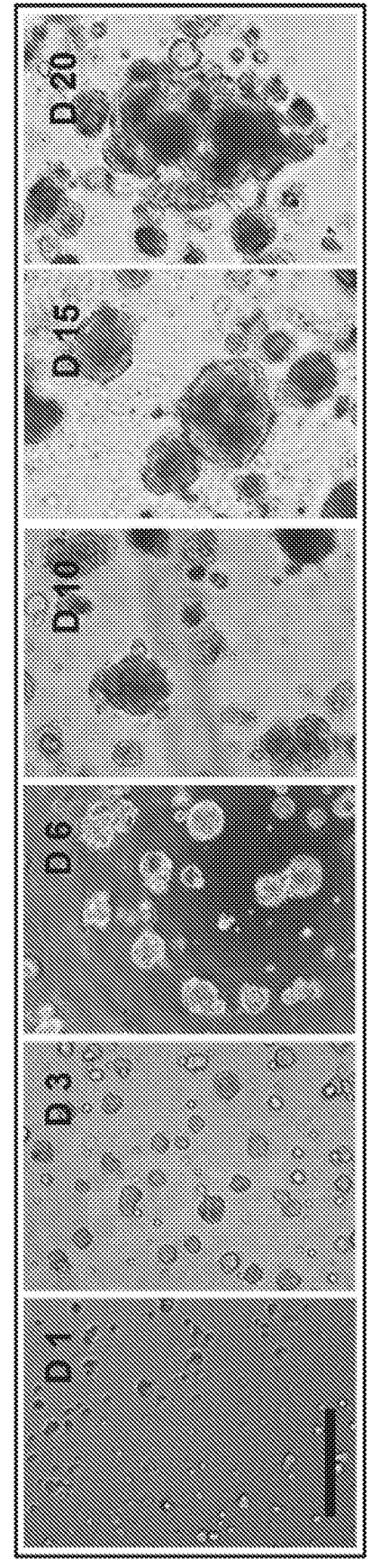
Figure 3C:
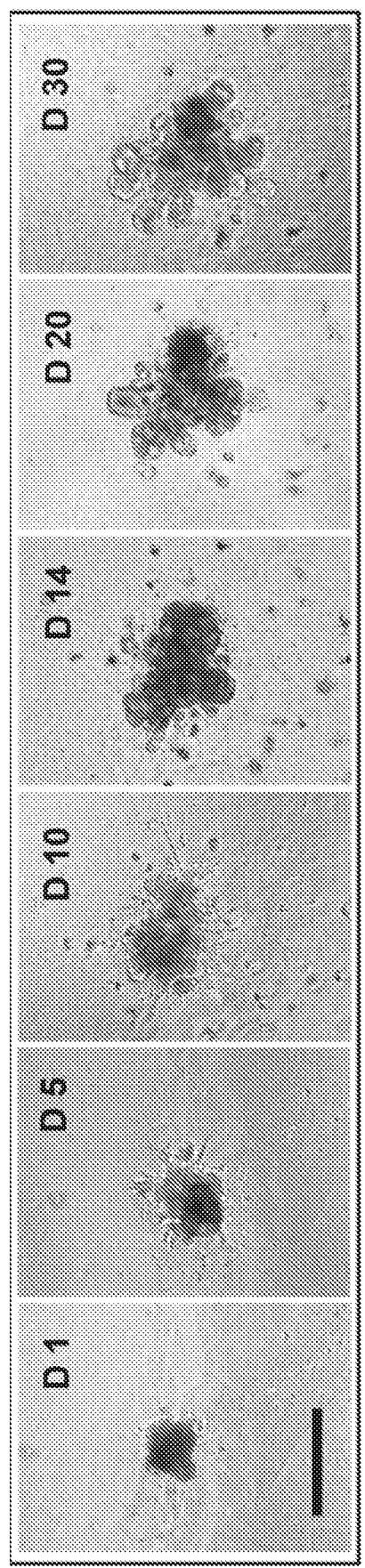

To generate mammary-like organoids, the Inventors developed a 3D culture method using a floating mixed gel composed of MATRIGEL® and Collagen I. The Inventors first tested the mixed gel using primary mouse and human mammary organoids. As shown in FIG. 3A, primary cultured organoids from 2-week old mice formed complex branched alveolar structures in the floating 3D culture in a 30-day period. Similarly, the majority of human mammary organoids formed alveolar structures with a less prominent branched component (FIG. 3B). The Inventors next grew 10-d mEBs in the mixed gel floated in EpiCult-B™ medium, which is commonly used in primary culture of human mammary epithelial cells (MECs). Given that 10-d mEBs may be predisposed to mammary commitment as suggested by gene and pathway analysis (see FIG. 2), the Inventors added pTHrP, a hormone involved in embryonic mammary development, to the culture and grew the organoids for 5 days, followed by supplementation of the culture with hydrocortisone, insulin, FGF10, and HGF to increase mammary cell specification. Then a lactogenic medium containing insulin, prolactin, and hydrocortisone was used to induce milk protein expression. As presented in FIG. 3C, alveolar mammary-like structures started to appear at day 10 of mEB 3D culture and this morphology became more pronounced at day 30. Together, the floating mixed gel culture system promotes the growth of mammary-like organoids from hiPSC-derived mEBs.

Figure 3D:
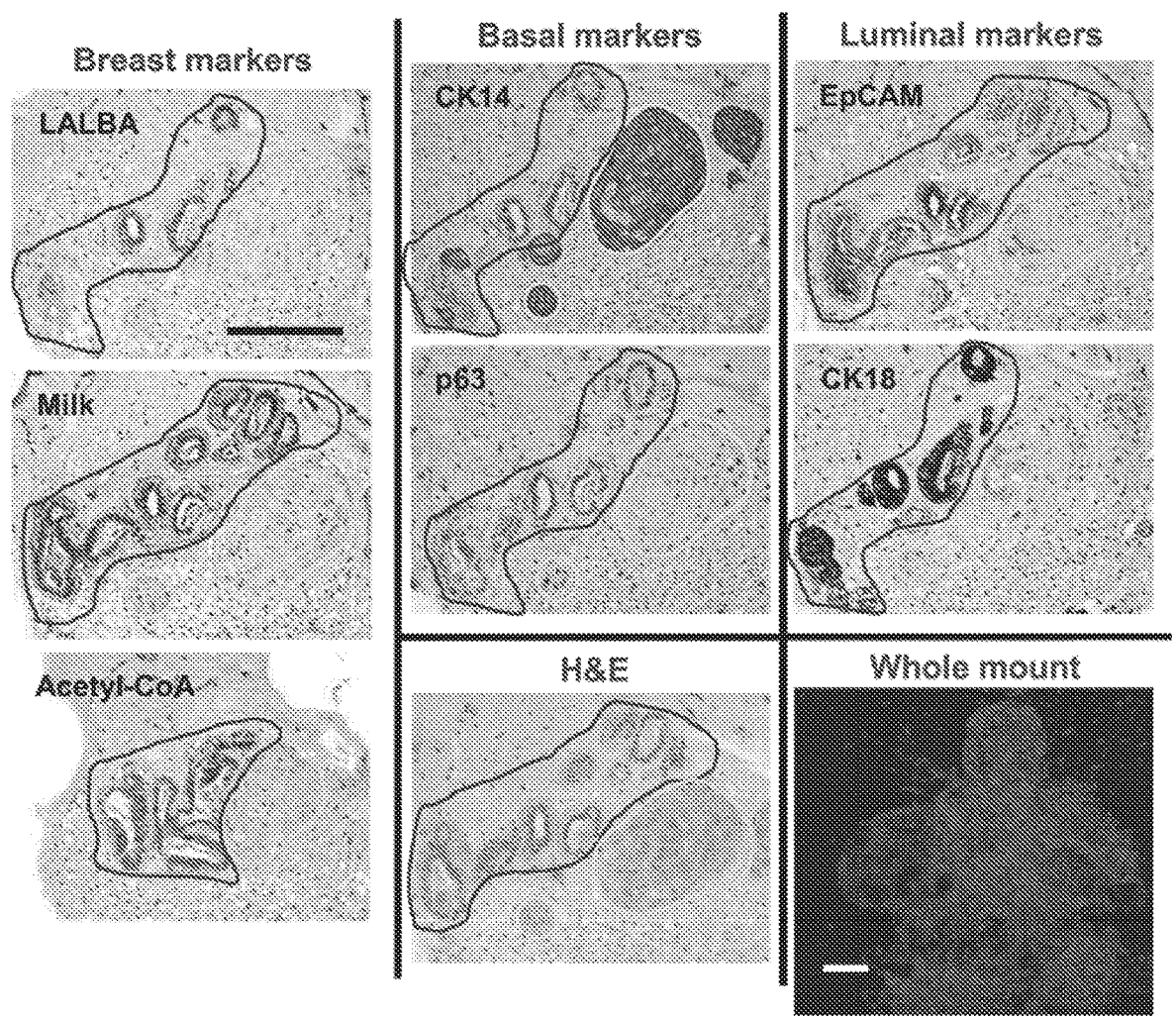
Figure 7C:
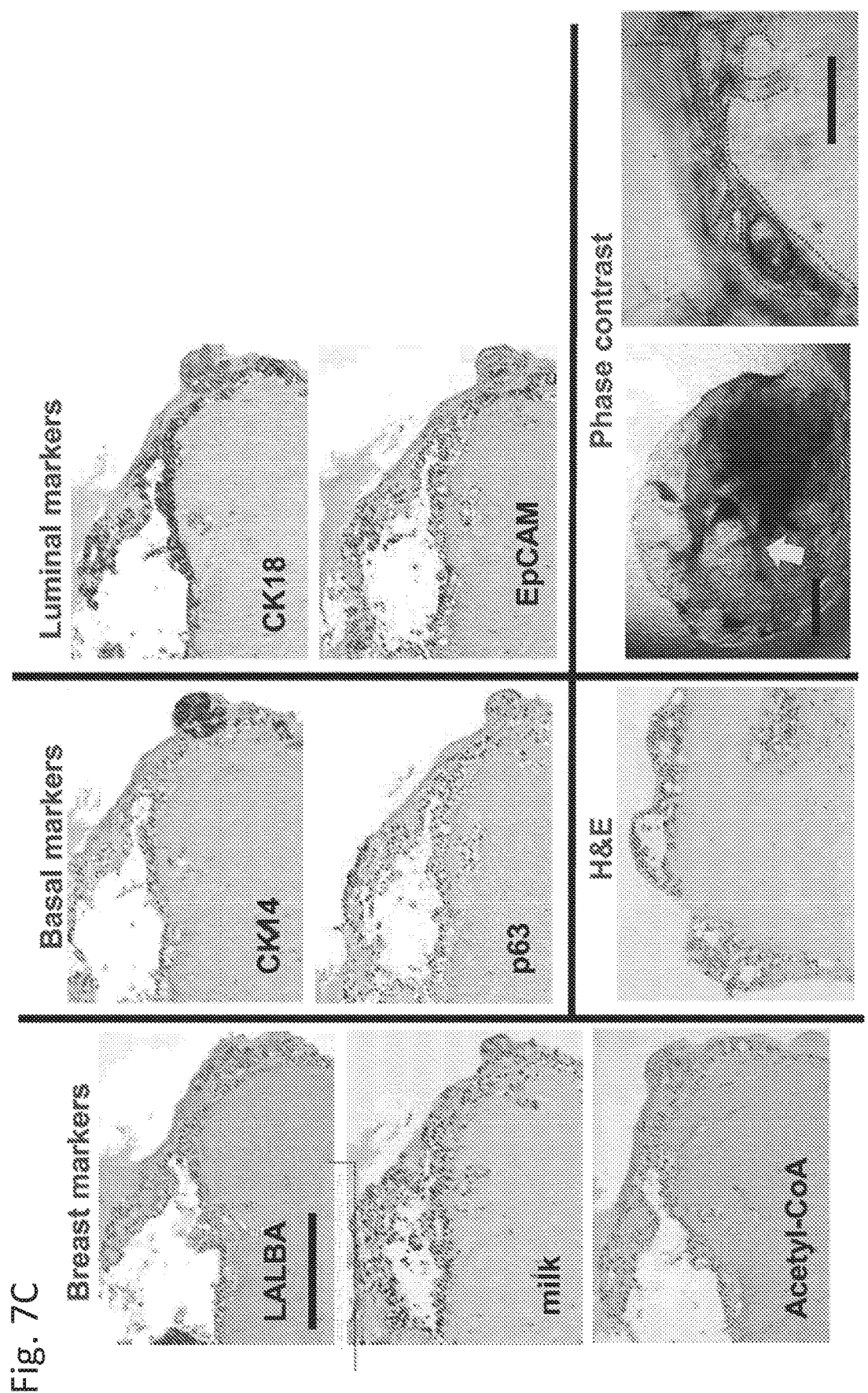
(FIG. 7C) Immunohistochemical staining of breast, basal and luminal marker expression in differentiated mammary-like structures (from 87iCTR hiPSC line). Yellow arrows: branch-like structures. Red broken lines: outline of branching out structure.
Figure 7D:
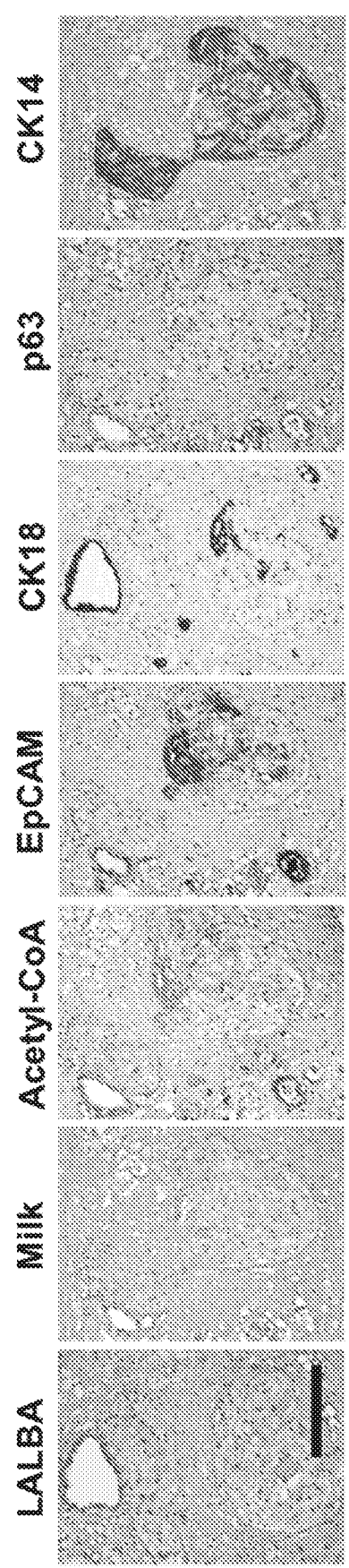
(FIG. 7D) Immunohistochemical staining of breast, basal, and luminal marker expression in organoids derived from 10-d mEBs without adding pTHrP in the initiation medium.
Figure 7E:
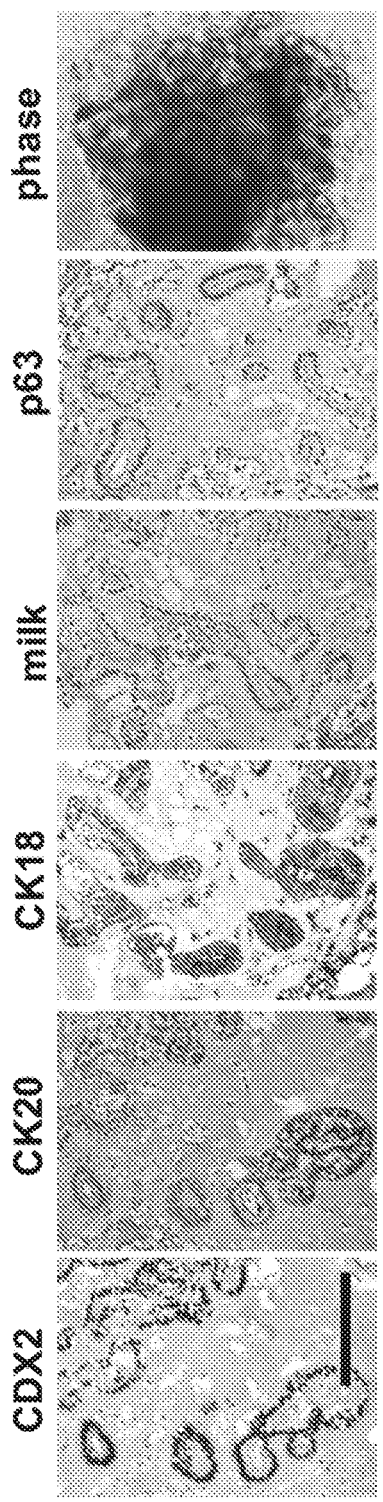
(FIG. 7E) Immunohistochemical staining of breast, basal and luminal marker expression in organoids derived from 21-d mEBs using the same three-stage protocol as used in 10-d mEBs culture. Bars: 100 µm.

To further investigate whether these organoids are of the mammary lineage, expression of widely used mammary markers was examined by immunohistochemistry. The Inventors found the structures were positive for breast markers (α-lactalbumin/LALBA, milk protein, and Acetyl-CoA), luminal epithelial markers (EpCAM and CK18), and basal markers (CK14 and P63) (FIG. 3D, red circles). These markers were also detected in normal human mammary gland tissue used as controls (FIG. 7A, B). Similar breast marker profiles were found in mammary-like branched structures from another iPSC line (FIG. 7C, yellow arrows). Of note, mEBs failed to form alveolar structures and exhibit mammary-associated marker expression in the absence of pTHrP (FIG. 7D). Furthermore, the late-stage mEBs (21-d), which did not express AP-2α and AP-2γ, gave rise to organoids expressing the intestinal markers CDX2 and CK20, but not milk and P63 proteins (FIG. 7E), when grown in the same 3D culture.

Figure 4H:
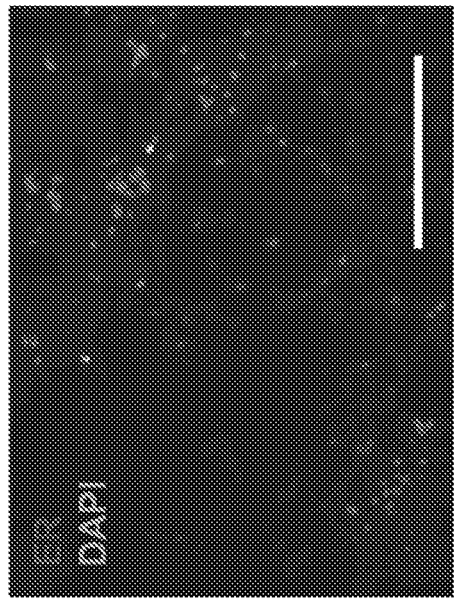
FIG. 4. Immunofluorescence staining of iPSC-differentiated mammary-like structures.
(FIG. 4A) Phase contrast (left) and immunostaining images of a mammary-like acinus. White broken lines show the edges of the acinus.
(FIG. 4B) Higher magnification images presenting the selected area in (FIG. 4A) as indicated by red broken lines. These images focus on the edge (left) and center (middle) of the structure. A merged image is shown on the right. Arrows 1-3 show P63-expressing cells.
(FIG. 4C) P63 and CK8 double staining in an acinar structure.
(FIG. 4D) P63 staining in primary human mammary epithelial cells. Nuclear staining (arrow 4) is positive signal. Cytoplasmic staining (arrow 5) is non-specific.
(FIG. 4E) EpCAM and CD49f co-staining in non-lactogenic mammary-like acini. Arrow 6: EpCAM$^-$/CD49f$^+$, arrow 7: EpCAM$^+$/CD49f, arrow 8: EpCAM$^+$/CD49f, arrow 9: EpCAM$^-$/CD49f. Right image: a stained whole organoid.
(FIG. 4F) Colony formation assays were performed using non-lactogenic mammary-like cells isolated from 3D culture. The colonies were stained using crystal valet and counted by the morphologies of colonies. The percentage of luminal-like, myoepithelial-like, and mixed-colonies was plotted. ER staining in lactogenic (FIG. 4G) and non-lactogenic (FIG. 4H) mammary-like cells are shown by immunofluorescence staining. Bars: 100 µm.
Figure 4F:
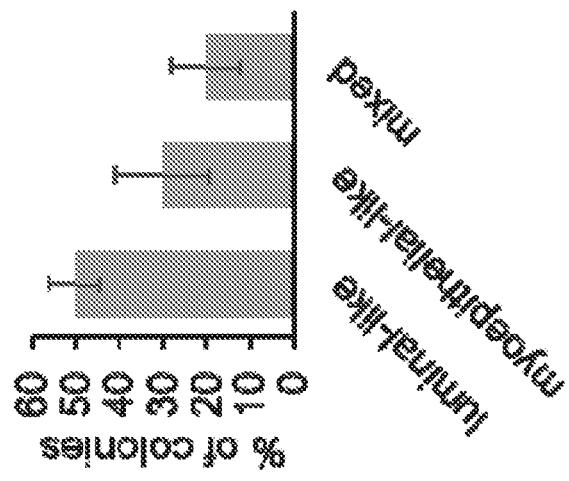
Figure 8A:
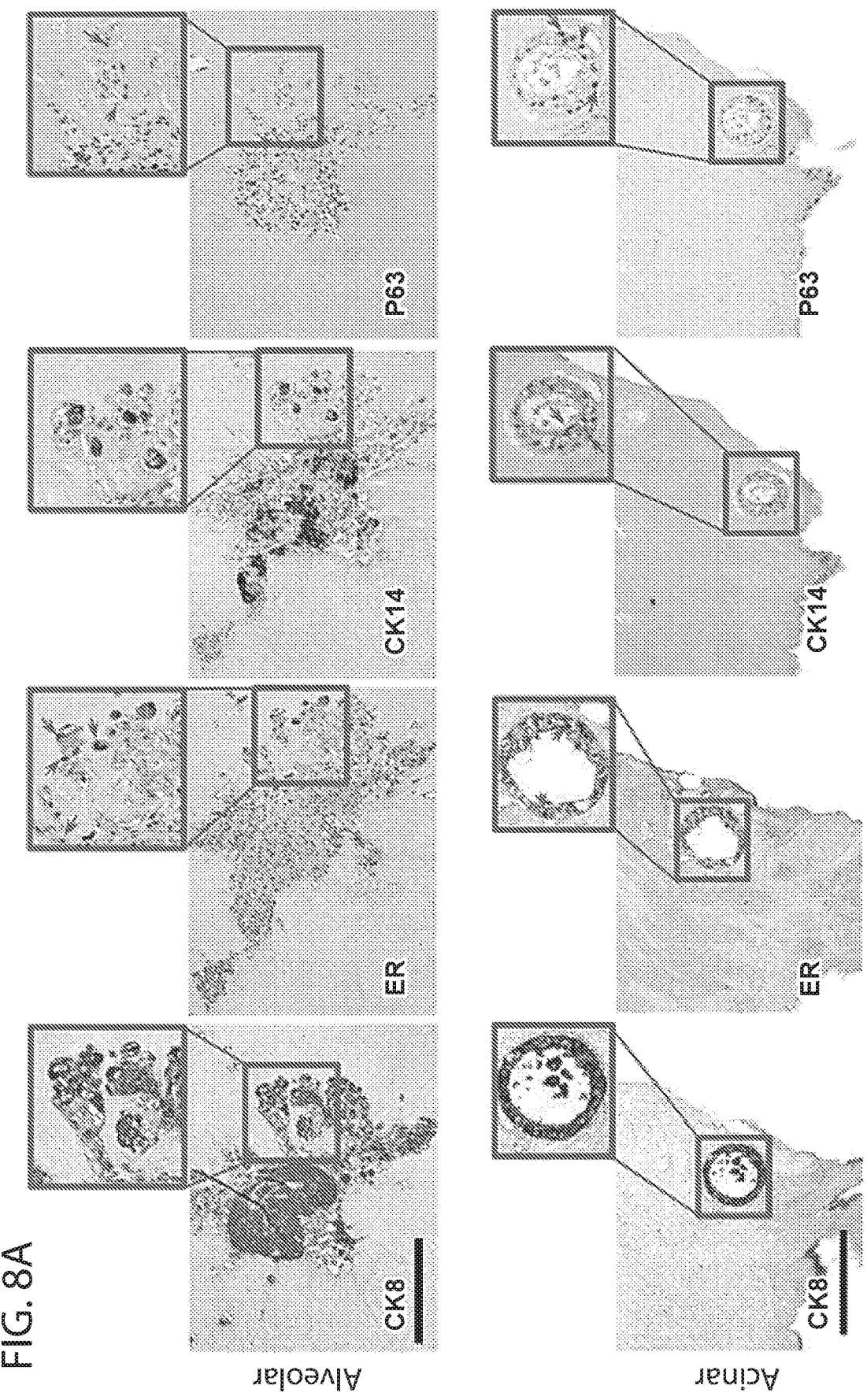
(FIG. 8A) Immunohistochemical staining of luminal marker (CK8), ER, basal marker (CK14 and P63) expression in mammary-like organoids. Pink arrows: positive cells.

Of note, the basal layer was not discernable in these structures. Because the basal layer is partially disrupted in the lactating human breast, the Inventors postulated that the lactogenic 3D culture condition might alter normal mammary epithelial structure. Thus luminal CK8 and basal P63 marker expression was examined by immunofluorescent staining in mammary-like organoids grown in non-lactogenic culture (see materials and methods). The Inventors observed acinar structures including luminal-like cells (CK8+) surrounded by a thin layer of basal-like cells (P63+) (FIG. 4A-D). Similarly, luminal and basal cell distributions in mammary-like alveolar and acinar structures were also observed by IHC staining (FIG. 8A). In addition, immunofluorescence staining revealed EpCAM+/CD49f, EpCAM+/CD49f, EpCAM−/CD49f+, and EpCAM−/CD49f− populations in these organoids (FIG. 4E), suggesting the presence of multiple cell populations. Furthermore, colony formation assays also showed that cells isolated from the organoids could yield luminal-like, myoepithelial-like, and mixed-morphological colonies (FIGS. 4F and 8B). Notably, a group of cells forming a coiled structure also expressed basal markers, but not breast or luminal markers (FIG. 3D, yellow circles), suggesting that non-mammary epithelial cells may also differentiate from non-neural ectoderm stem cells in the Inventors' culture system.

Figure 4G:
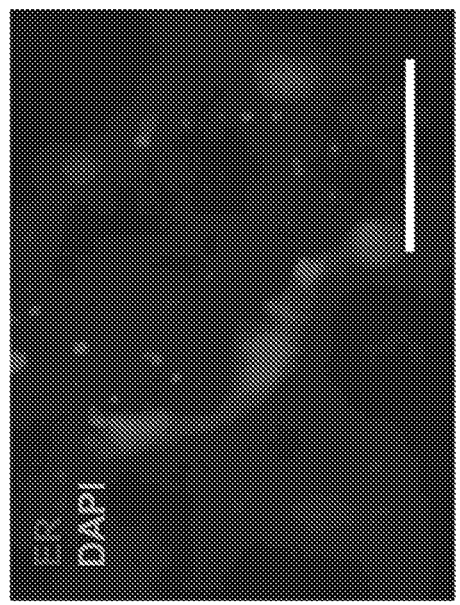

It was also noted that estrogen receptor (ER) expression was not detected in mammary-like cells under lactogenic conditions (FIG. 4G), which may be due to the inhibition of ER expression under lactogenic conditions. Indeed, immunohistochemical staining showed that ER expression was drastically decreased in human lactating breast tissue compared to non-lactating tissue (FIG. 8C). Consistent with these results, ER expression was induced in mammary-like cells under non-lactogenic conditions (FIGS. 4H and 8A). In summary, the Inventors' results suggest that the Inventors' semi-solid floating matrix culture system facilitates the differentiation of iPSCs into functional mammary-like organoids.

Example 8

DISCUSSION

Despite advances in mammary gland biology and breast cancer research and successful directed differentiation of iPSCs into organoids/tissues, such as neuron, lung, and gut, in vitro generation of mammary organoids from human iPSCs has not been reported. A previous study shows partial in vitro mammary phenotype differentiation from bovine. The Inventors' study represents the first successful generation of mammary-like cells and organoid structures from human iPSCs.

The Inventors initially attempted the well-established EB-based approach for pluripotent stem cell differentiation in order to enrich non-neural or surface ectoderms, the precursors of mammary stem cells. It turned out that EBs preferentially enrich for neural lineage cells. Interestingly, the MammoCult™ medium, which has been commonly used to enrich breast stem cells, directed the iPSC differentiation toward the non-neural ectoderm cell fate. Similar to EB, mEB differentiation undergo two stages which sequentially produce solid spheres and cystic spheres. Immunohistochemical staining, western blotting, and cDNA microarray analysis suggests that 10-d mEBs harbor high levels of non-neural stem cell markers, but not neural ectoderm or mesoderm markers. Importantly, 10-d mEBs are susceptible to culture conditions leading to the formation of mammary-like cells and organoids.

The development of normal human mammary glands are controlled by cytokines and hormones, such as insulin, hydrocortisone, FGF10 and HGF, all well-known for mammary epithelial cell survival and differentiation. pTHrP and BMP4 are also required for the commitment of embryonic mammary lineage. Terminal differentiation of mammary epithelial acinus requires lactogenic hormones including prolactin, insulin and glucocorticoids. Based on the published methods for 3D culture of human mammary epithelial cells, the Inventors developed a floating mixed gel system to induce mammary cell differentiation from iPSCs. Of note, Collagen I (1 mg/mL) is included in the 3D culture as it may yield a similar stiffness as in the normal mammary gland, at about 170 Pa. The alveolar structures observed in this 3D culture expressed breast, luminal and basal markers, suggesting mammary-like cells are induced. In non-lactogenic mammary-like cells, ER expression and organized basal-luminal structures were also observed. These results have suggested mammary-like differentiation from iPSCs in the Inventors' system.

Interestingly, the Inventors' observations described confirm the utility of iPSC as a platform to study mammary development and maturation. This includes the described results of multiple cell populations, formation assays yielding luminal-like, myoepithelial-like, and mixed-morphological colonies, induction of structures such as aveolar and acinar features and functional acquisition (e.g. lactogenesis). In this aspect, iPSCs faithfully recapitulate a multiplicity of features that occur during in vivo developmental and maturation stages. By contrast, primary breast cells, which have been grown in vitro merely expand existing cellular populations from biopsy samples, and lack the multiple properties existing within developing and maturing breast organ. In this aspect, iPSC-derived mammary cells and mammary cell organoids can present a great deal more complexity with higher relevancy for modeling in a way that primary breast cells cannot.

In conclusion, the Inventors have developed a novel two-step method of directing mammary differentiation from human iPSCs. The iPSC-derived mammary-like organoids can be used to build in vitro models for pinpointing the precise effects of various factors on mammary cell transformation and breast cancer development and for personalized bioengineering of mammary tissue. Future research is warranted to elucidate the effect of individual hormones and growth factors on iPSC differentiation into mammary cells and to refine the culture system for generating two-layer mammary ductal structures in vitro. The Inventors hope the Inventors' novel findings can open up new avenues for developing iPSC-based approaches to solve critical questions in human mammary gland and breast cancer development challenging for conventional methodology.

Example 9 hiPSC Culture

Fibroblast-derived (OOiCTR-n2 and 83iCTR-n1) and blood-derived (87iCTR) hiPSC lines used in this study were generated at Cedars-Sinai Medical Center approved by the Institutional Review Board (IRB) (Sareen et al., 2014a; Sareen et al., 2014b). The characterization and karyotyping were performed as previously described (Sareen et al., 2014a). The hiPSC lines were maintained using a feeder-free system with growth factor-reduced BD MATRIGEL® matrix and maintained in chemically-defined mTeSR1 medium (StemCell technologies Inc., Vancouver, Canada).

Example 10

EB Culture

For EB culture, hiPSCs were lifted by Accutase (Innovative Cell Technologies, Inc., San Diego, CA) and suspended in EB medium (IMDM supplemented with 17% KOSR, 1% NEAA, 0.1% β-ME, and 1% PSA), 5×103/well were seeded in 384-well plate. The plate was spun at 1,400 rpm at 4° C. for 7 min. Plate was put in 37° C. incubator overnight. EBs were collected the next day and pooled into a 100 mm ultra-low attachment plates (Corning Incorporated, Corning, NY). Medium was changed every 3 days.

Example 11

Culture of MammoCult-Derived Embryoid Bodies (mEBs)

To generate mEBs, iPSCs were lifted using Accutase (Innovative Cell Technologies, Inc., San Diego, CA) and suspended in the complete MammoCult™ medium (Stem-Cell Technologies), which was composed of the basal medium, proliferation supplements, heparin (4 µg/mL), and hydrocortisone (0.48 µg/mL).

Example 12

Isolation and Culture of Mouse and Human Mammary Organoids

Mouse mammary epithelial cells were prepared as previously described (Stingl et al., 2006). The mammary glands from 2-week (wk) old mice were minced and digested overnight at 37° C. in EpiCult B™ Mouse Medium (Stem-Cell technologies) supplemented with 5% fetal bovine serum (FBS, Sigma) containing 300 U/ml collagenase and 100 U/ml hyaluronidase (StemCell technologies). After dissociation, cells were pelleted at 350×g for 5 min and filtered through a 40-µm mesh. Mammary organoids were collected and subjected to 3D culture. Organoids were embedded in MATRIGEL® (BD Biosciences, San Diego, CA) (2.5 mg/mL)/Collagen I (Advanced Biomatrix, Carlsbad, CA) (1 mg/mL) mixed gel. Culture medium was composed of DMEM/F12 (Lonza, Walkersville, MD), 5% FBS, 0.1% v/v Insulin-Transferrin-Sodium (ITS) Selenite media supplement (1000× stock, Sigma-Aldrich), 9 nM FGF2 (Peprotech), and 9 nM FGF10 (Peprotech) (Mroue and Bissell, 2013). Human mammary epithelial organoids were isolated from prophylactic mastectomy, following the established method (Labarge et al., 2013). Briefly, epithelial areas from the samples were separated and chopped into 1-3 mm squares. Tissue was digested using the mixture of DMEM/F-12, 10 µg/ml insulin, antibiotics, 10% FCS, 200 U/ml crude collagenase (Sigma), and 100 U/ml hyaluronidase (Sigma) with 3600 rotation at 8 rpm overnight at 37° C. The digested pellets were collected by centrifugation followed by passing through 100 and 40 µm strainers (Corning, Durham, NC). Fresh isolated organoids were embedded in MATRIGEL®/Collagen I (1 mg/mL) mixed gel in complete EpiCult B™ medium supplemented with hydrocortisone (1 µg/ml), insulin (10 µg/ml), FGF10 (50 ng/ml) and HGF (50 ng/ml) for 3D culture.

Example 13

Mammary-Like Organoid Differentiation 3D culture was performed by embedding 10-d mEBs in mixed MATRIGEL® (2.5 mg/mL)/Collagen I (1 mg/mL) gel on the Nunclon delta surface culture plate (Sigma). Mixed gel was made by mixing 3 portions of 10.1 mg/ml MATRIGEL® with 1 portion of 4 mg/ml Collagen I. The final concentration of MATRIGEL® and Collagen I in the mixed gel was 2.5 mg/mL and 1 mg/mL (Krause et al., 2012), respectively. After being solidified, the mixed gel was detached and additional culture medium was added for floating 3D culture. The culture medium was changed every 3 days. To induce mammary commitment, floating gels were cultured in complete EpiCult B medium supplemented with parathyroid hormone (pTHrP, 100 ng/ml) for 5 days. To induce branch and alveolar differentiation, the gels were cultured in complete EpiCult B medium supplemented with hydrocortisone (1 µg/ml), insulin (10 µg/ml), FGF10 (50 ng/ml), and HGF (50 ng/ml) for 20 days. To induce milk protein expression in lactogenic medium, prolactin (10 µg/ml), hydrocortisone (1 µg/ml), and insulin (10 µg/ml) were added to complete EpiCult B medium supplemented with 10% Fetal Bovine Serum (FBS) for 5 days. All growth factors were recombinant human proteins and purchased from Peprotech (Rocky Hill, NJ). Hormones were purchased from Sigma. Of note, implanting GFP-labeled iPSC/mEBs into the cleared fat pads of NSG mice did not lead to ductal formation, which may be due to a lack of embryonic microenvironment cues in the mammary tissue, which are required for pluripotent stem cells to differentiate toward the mammary lineage.

Example 14

Colony Formation Assays

Colony formation assays were performed as previously described (Martignani et al., 2015). Briefly, non-lactogenic mammary-like cells were isolated from 3D culture using Collagenase (0.1 U/mL)/Dispase (0.8 U/mL) (Sigma). Cells were seeded at 1×103cells/well in 6 well plate and kept in culture for 14 days using complete EpiCult B™ medium on a layer of mitomycin C (Sigma)-treated NIH 3T3 cells. The colonies were visualized by Wright-Giemsa (Sigma) staining.

Example 15

Immunohistochemical (IHC) Staining

Suspension or 3D culture was fixed with 10% phosphate-buffered formalin and embedded in paraffin. Tissue or cell culture blocks were cut into 4-µm thick sections for immunostaining. Slides were deparaffinized and rehydrated by xylene and gradient ethanol, respectively. Antigen retrieval was performed using microwave pretreatment and 0.01 M sodium citrate buffer (PH6) for all antibodies (Vector laboratories, Burlingame, CA). Primary antibodies used in the staining were PAX6 (1:200, Santa Cruz, #sc-81649), AP-2α (1:200, Santa Cruz, #sc-12726), Acetyl-CoA (1:100, Cell signaling, #3676), CK18 (1:200, Abcam, #ab181597), CK14 (1:200, Abcam, #ab7800), EpCAM (1:150, Abcam, #ab8666), milk (1:500 (Martignani et al., 2010), Nordic, Eindhoven, The Netherlands, #3976), P63 (1:100, Biocare, clone 4A4, Concord, CA, #CM163), LALBA (1:1500, Sigma, #HPA029856), CDX2 (1:100, Biocare, Concord, CA, #CM226), ER (1:100, Biocare, #ACA301), and CK20 (1:200, Biocare, #CM062) were applied to the sections. The signal was visualized using the VECTASTAIN ABC Systems (Vector laboratories). Counterstaining was performed with Mayer's hematoxylin (Sigma). Appropriate positive and negative controls were run simultaneously. Photomicrographs were obtained using an Olympus BX51 light microscope (Olympus).

Example 16

Immunofluorescence Staining

Cells were fixed with 4% paraformaldehyde, permeabilized with 0.5% Triton X-100 for 10 min, and blocked with 3% bovine serum albumin for 30 min at room temperature. Tissue blocks were cut into 4-µm thick sections for the following staining. Slides were deparaffinized and rehydrated as described above. The same antigen retrieval method as in IHC was used. After blocking, cells were incubated overnight at 4° C. with primary antibodies. Primary antibodies were AP-2α (1:200, Santa Cruz, #sc-12726), AP-2γ (1:100, Abcam, #ab76007), CK8 (1:200, Abcam, #ab9032), CK18 (1:200, Abcam, #ab181597), OTX2 (1:100, R&D, #AF1979), TUJ1 (1:200, Promega, #G7121), CK14 (1:200, Abcam, #ab7800), milk (1:500, Nordic, #3676), EpCAM (1:100, Thermo Fisher, #MA5-12436), CD49f (1:200, R&D Biosciences, #MAB13501), P63 (rabbit polyclonal targeting 125 and 415 amino acids) (Genetex, Irvine, CA, #GTX102425), ER (1:100, Biocare, #ACA301), and CSN2 (1:200, Abcam, #ab47972). Alexa 594—(red, Molecular Probes, Eugene, OR) and Alexa 488—(green, Molecular Probes) conjugated secondary antibody was used to visualize the staining (1:200). Following three washes with PBS, slides were mounted with the VECTASHIELD mounting medium (Vector Laboratories, Burlingame, CA). Prior to mounting, slides were incubated with 2 µM 4',6-diamidino-2-phenylindole (DAPI) (Molecular Probes) for 10 min at 37° C. to stain the nuclei. The fluorescence images were taken using the EVOS FL Auto Cell Imaging System (Thermo Fisher Scientific, NY, USA).

Example 17

Confocal Microscopy

The mammary-like organoids were fixed with 4% paraformaldehyde and permeabilized with 0.5% Triton X-100 as previously described. Phalloidin-AF555 (Thermal fisher) was used to stain F-actin. DAPI was used to stain nuclei. After three times washing, the organoids were allowed to dry overnight in dark. The slides were mounted using ProLong Gold Antifade Mountant (Thermo Fisher Scientific). The images were taken using confocal microscope (Leica). Z-stack images were processed using Leica application suite software.

Example 18

Western Blotting

Proteins were extracted from human breast cancer cells using RIPA lysis buffer (Sigma-Aldrich) and protein concentration was determined by the BCA Protein Assay Kit (Thermo). Proteins (40 µg) were separated on 4-20% gradient gels and transferred onto PVDF membranes using Trans-Blot Turbo transfer pack (Bio-Rad) and Trans-Blot Turbo transfer system (Bio-Rad). Membranes were blocked in Odyssey blocking buffer (LI-COR) and incubated with primary antibodies overnight at 4° C. The primary antibodies were FOXA2 (Abcam, #ab89997), T/Brachyury (Novus, #NBP2-24676), GATA4 (Novus, #NBP2-24585), P63 (Genetex, #GTX102425), AP-2α (Santa Cruz, #sc-12726), FOXG1 (Abcam, #ab18259), SOX11 (Abcam, #ab170916), AP-2γ (Abcam, #ab76007), CK8 (Abcam, #ab53280), CK18 (Abcam, #ab133263), OCT4 (Stem cells, #60059), SOX2 (Stem cells, #60055), Nanog (Stemgent, Lexington, MA, #09-0020), TUJ1 (Promega, #G7121), p-p 65 Ser536 (Cell Signaling, #3033), non-phospho Ser33/37/Thr41 β-catenin (Cell Signaling, #13537), PAX6 (Thermo Fisher, #13B10-1A10), GAPDH (Santa Cruz, #sc-47724). The membranes were then incubated with IRDye 680CW or IRDye 800CW secondary antibodies (LI-COR) for 1 hour at room temperature. The membranes were scanned using the Odyssey infrared imaging system (LI-COR).

Example 19 cDNA Microarray

Total RNA from spheres and iPSCs was extracted using the RNeasy Mini kit (Qiagen, Valencia, CA, USA) according to the manufacturer's instructions. RNA quantity and purity was assessed by measurement of OD260/280 using a NanoDrop ND-1000 spectrophotometer (Thermo Fisher Scientific). Gene expression profiling was conducted using Illumina Human HT-12 v4 BeadChip. Direct Hybridization Assay was used and chips are scanned on the HiScan system. The cDNA microarray data were log 2-transformed and quantile normalized.

Example 20

Pathway and Network Analysis by IPA

Analytics tools "Bio Function analysis", "Upstream Regulator Analysis" and "Regulatory Networks" were provided by Ingenuity Pathway Analysis software (IPA, QIAGEN Redwood City, CA, USA). The "Bio Functions analysis" is to predict the downstream biological processes which are increased or decreased based on input data. The "Upstream Regulator analysis" is based on prior knowledge of expected effects between transcriptional regulators and their target genes stored in the Ingenuity Knowledge Base. The analysis examines how many known targets of each transcription regulator are present in the user's dataset, and also compares their direction of change (i.e. expression in the experimental sample(s) relative to control) to what is expected from the literature in order to predict likely relevant transcriptional regulators. If the observed direction of change is mostly consistent with a particular activation state of the transcriptional regulator ("activated" or "inhibited"), then a prediction is made about that activation state. Comparison analysis between input datasets is to visualize trends and similarities. The activation z-score is used to infer likely activation states of upstream regulators based on comparison with a model that assigns random regulation directions. Connections within selected upstream regulators and their regulated (downstream) genes are further displayed by "regulatory network". "Bio Function filter" is applied onto networks to further uncover the intrinsic connections within predicted functions and the networks. All analyses were carried out with differentially expressed genes (mEBs/iPSCs). Differentially expressed genes were imported with the following cut-offs applied: fold change $\geq 1.5$ and $\leq -1.5$ as well as t-test p-value <0.05.

Example 21

Statistical Analysis

Values represent mean±standard deviation (SD) of samples measured by three independent experiments. Quantitative data were analyzed using the Student's t test and two-tailed distribution. Correlations between groups were analyzed by calculating the Pearson's correlation coefficient (r) using the IBM SPSS statistics 20.0 program. Log-rank tests were performed to determine statistical significance. A P-value <0.05 was considered significant.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are techniques for producing mammary cells and organoids, culture reagents, and methods of utilizing differentiated mammary cells for prognostic and/or diagnostic panels, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating mammary cells, comprising:
culturing human induced pluripotent stem cells (hiPSCs) in a serum-free culture medium enriching non-neural ectoderm cells, the serum-free culture medium comprising a basal medium, proliferation supplements, heparin, and hydrocortisone for the culture of non-neural ectoderm cell-containing mammospheres, for about 8-12 days to generate embryoid bodies (EBs) expressing non-neural ectoderm stem cell markers AP-2γ, CK8 and CK18, wherein the EBs do not express neural ectoderm stem cell markers OTX and SOX11; and
differentiating the EBs into mammary cells comprising breast cells, luminal cells, and basal cells by culturing in a differentiation medium supplemented with pTHrP from day 1 to day 5, followed by culturing in the differentiation medium supplemented with hydrocortisone, insulin, FGF10, and HGF for 3D culture for about 23-27 days, the differentiation medium being a serum-free culture medium for the culture of mammary luminal and myoepithelial cells.

2. The method of claim 1, wherein OTX comprises OTX2.

3. The method of claim 1, wherein differentiating the EBs into mammary cells comprises culturing in the presence of a substrate.

4. The method of claim 3, wherein the substrate comprises Collagen I and/or solubilized basement membrane matrix secreted by Engelbreth-Holm-Swarm (EHS) mouse sarcoma cells.

5. The method of claim 1, wherein pTHrP is at a concentration of about 50 ng/ml-150 ng/ml.

6. The method of claim 1, wherein the breast cells express one or more markers selected from the group consisting of: α-lactalbumin/LALBA, milk protein, and Acetyl-CoA.

7. The method of claim 1, wherein the luminal cells express one or more markers selected from the group consisting of: EpCAM and CK18.

8. The method of claim 1, wherein the basal cells express one or more markers selected from the group consisting of: CK14 and P63.

9. The method of claim 1, wherein the mammary cells are lactogenic mammary cells.

10. The method of claim 9, wherein differentiating the EBs to induce formation of the lactogenic mammary cells comprises culturing mammary organoids in a lactogenic medium containing insulin, prolactin and/or hydrocortisone.

11. A method of generating mammary cell organoids, comprising:
culturing human induced pluripotent stem cells (hiPSCs) in a serum-free culture medium enriching non-neural ectoderm cells, the serum-free culture medium comprising a basal medium, proliferation supplements, heparin, and hydrocortisone for the culture of non-neural ectoderm cell-containing mammospheres, for about 8-12 days to generate embryoid bodies (EBs) expressing non-neural ectoderm stem cell markers AP-2γ, CK8 and CK18, wherein the EBs do not express neural ectoderm stem cell markers OTX and SOX11; and
differentiating the EBs into mammary cell organoids comprising breast cells, luminal cells, and basal cells by culturing in a differentiation medium comprising one or more substrates and supplemented with pTHrP from day 1 to day 5, followed by culturing in the differentiation medium supplemented with hydrocortisone, insulin, FGF10, and HGF for 3D culture for about 23-27 days, the differentiation medium being a serum-free culture medium for the culture of mammary luminal and myoepithelial cells,
wherein the one or more substrates comprise Collagen I, solubilized basement membrane matrix secreted by Engelbreth-Holm-Swarm (EHS) mouse sarcoma cells, or both.

12. The method of claim 11, wherein OTX comprises OTX2.

13. The method of claim 11, wherein Collagen I is at a concentration of about 0.5-1.5 mg/mL and/or the solubilized basement membrane matrix is at a concentration of about 1.5-3.5 mg/mL.

14. The method of claim 11, wherein the breast cells express one or more markers selected from the group consisting of: α-lactalbumin/LALBA, milk protein, and Acetyl-CoA, the luminal cells express one or more markers selected from the group consisting of: EpCAM and CK18, and the basal cells express one or more markers selected from the group consisting of: CK14 and P63.

15. The method of claim 11, wherein the mammary cell organoids are lactogenic mammary cell organoids.

16. The method of claim 15, wherein differentiating the EBs to induce formation of the lactogenic mammary cell organoids comprises culturing mammary organoids in a lactogenic medium containing insulin, prolactin and/or hydrocortisone.

17. The method of claim 11, wherein the mammary cells organoids comprise aveolar structures.

18. The method of claim 11, wherein iPSCs are cultured in the serum-free culture medium for about 10 days, and the EBs are differentiated in the differentiation medium for about 30 days.

19. A method of generating mammary cells, comprising:
culturing human induced pluripotent stem cells (hiPSCs) in a serum-free culture medium enriching non-neural ectoderm cells, the serum-free culture medium comprising a basal medium, proliferation supplements, heparin, and hydrocortisone for the culture of non-neural ectoderm cell-containing mammospheres, for about 8-12 days to generate embryoid bodies (EBs) expressing non-neural ectoderm stem cell markers AP-2γ, CK8 and CK18, wherein the EBs do not express neural ectoderm stem cell markers OTX and SOX11;
differentiating the EBs into mammary cells comprising breast cells, luminal cells, and basal cells by culturing in a differentiation medium comprising hydrocortisone, insulin, FGF10, and HGF for 3D culture for about 28-32 days, wherein the EBs are cultured in the presence of pTHrP at a concentration of about 50 ng/ml-150 ng/ml from day 1 to day 5, the differentiation medium being a serum-free culture medium for the culture of mammary luminal and myoepithelial cells; and
differentiating the mammary cells to induce formation of the lactogenic mammary cells comprising culturing the mammary cells in the presence of insulin, prolactin and/or hydrocortisone.

* * * * *